United States Patent [19]
Small et al.

[11] Patent Number: 5,444,541
[45] Date of Patent: Aug. 22, 1995

[54] METHODS FOR PHOTOACOUSTICALLY ANALYZING CHEMICALS AND CHEMICAL REACTIONS USING PHOTOACTIVE PARTICLE-EMITTING COMPOUNDS

[75] Inventors: Jeanne R. Small; Enoch W. Small, both of Cheney, Wash.

[73] Assignee: Eastern Washington University, Cheney, Wash.

[21] Appl. No.: 197,689

[22] Filed: Feb. 16, 1994

[51] Int. Cl.$^6$ ............................................. G01N 21/75
[52] U.S. Cl. ................................................. 356/432
[58] Field of Search ........................................ 356/432

[56] References Cited

U.S. PATENT DOCUMENTS

4,303,343  12/1981  Patel et al. .
4,557,137  12/1985  Kitamori et al. .

FOREIGN PATENT DOCUMENTS

0233403B1  11/1986  European Pat. Off. .
0233403A1  11/1986  European Pat. Off. .
WO92/08720  5/1992  WIPO .

OTHER PUBLICATIONS

L. M. Tolbert, L. C. Harvey, et al., "Excited-State Proton Transfer from Hydroxyalkylnaphthols", 1993, pp. 13335–13340.

S. Khan, M. Meister, et al., "Constraints on Flagellar Rotation", 1985, pp. 645–656.

M. Irie, "Light-Induced Reversible pH Change", 1983, pp. 2078–2079.

J. E. T. Corrie and D. R. Trentham, "Caged Nucleotides and Neurotransmitters", 1993, pp. 243–305.

C. L. Norris and K. S. Peters, "A Photoacoustic Calorimetry Study of Horse Carboxymyoglobin on the 10-Nanosecond Time Scale", 1993, pp. 1660–1665.

J. A. McCray, L. Herbette, et al., "A New Approach to Time-Resolved Studies of ATP-Requiring Biological Systems: Laser Flash Photolysis of Caged ATP", 1980, pp. 7237–7241.

J. A. McCray and D. R. Trentham, "Rapid Release of Protons by Photolysis of a Biologically Inert Precursor, 2-Hydroxyphenyl 1-(2-Nitro)Phenylethyl Phosphate, A 'Caged Proton'", 1985, p. 406a.

D. R. Ort and W. W. Parson, "Enthalpy Change During the Photochemical Cycle of Bacteriorhodopsin", 1979, pp. 355–364.

R. C. J. Neuman, W. Kauzmann, et al., "Pressure Dependence of Weak Acid Ionization in Aqueous Buffers", 1973, pp. 2687–2691.

J. Feitelson and D. C. Mauzerall, "Wide-Band, Time-Resolved Photoacoustic Study of Electron-Transfer Reactions: Photoexcited Magnesium Porphyrin and Quinones", 1993, pp. 8410–8413.

C. K. N. Patel and A. C. Tam, "Pulsed Optoacoustic Spectroscopy of Condensed Matter", 1981, pp. 517–550.

L. J. Rothberg, J. D. Simon, et al., "Pulsed Laser Photoacoustic Calorimetry of Metastable Species", 1983, pp. 3464–3468.

D. R. Ort and W. W. Parson, "Flash-Induced Volume Changes of Bacteriorhodopsin-Containing Membrane Fragments and Their Relationship to Proton Movements and Absorbance Transients", 1978, pp. 6158–6164.

(List continued on next page.)

*Primary Examiner*—Richard A. Rosenberger
*Attorney, Agent, or Firm*—Wells, St. John, Roberts, Gregory & Matkin

[57] ABSTRACT

Methods for analyzing chemicals and chemical reactions on the nanosecond to microsecond time scales. A liquid sample includes a solvent and chemical(s) of interest. A proton-emitting compound is included in the sample. A laser or other stimulating electromagnetic pulse is beamed onto the sample. The beam causes volumetric changes in the sample which produce pressure waves. The pressure waves are sensed by an acoustic detector. Beam energies and acoustic information are analyzed to extract information from the acoustic signal which is indicative of volumetric changes caused by conformational changes in the chemical of interest or by reactions between molecules.

12 Claims, 13 Drawing Sheets

OTHER PUBLICATIONS

Jeanne E. Rudzki, "The Photochemical Dynamics and Energetics of Phodopsin and Myoglobin", 1985, pp. 1–227.

J. A. Westrick, J. L. Goodman, et al., "A Time-Resolved Photoacoustic Calorimetry Study of the Dynamics of Enthalpy and Volume Changes Produced in the Photodissociation of Carbon Monoxide From Sperm Whale Carboxymyoglobin", 1987, pp. 8313–8318.

K. S. Peters, T. Watson, et al., "Time-Resolved Photoacoustic Calorimetry: A Study of Myoglobin and Rhodopsin", 1991, pp. 343–362.

E. Shimoni, Y. Tafadia, et al., "Gaugement of the Inner Space of the Apomyoglobin's Heme Binding Site by a Single Free Diffusing Proton. I. Proton in the Cavity", 1993, pp. 472–479.

E. Shimoni, E. Nachliel, et al., "Gaugement of the Inner Space of the Apomyglobin's Heme Binding Site by a Single Free Diffusing Proton. II. Interaction with a Bulk Proton", 1993, pp. 480–483.

S. E. Braslavsky and G. E. Heibel, "Time-Resolved Photothermal and Photoacoustic Methods Applied to Photoinduced Processes in Solution", 1992, 1381–1410.

M. Eigen, "Methods for Investigation of Ionic Reactions in Aqueous Solutions with Half-Times as Short as $10^{-9}$ Sec: Application to Neutralization and Hydrolysis Reactions", 1954, pp. 194–205.

K. K. Smith, K. J. Kaufmann, et al., "Picosecond Proton Ejection: An Ultrafast pH Jump", 1979, pp. 522–527.

E. Pines and D. Huppert, "pH Jump: A Relaxational Approach", 1983, pp. 4471–4478.

H. M. Chen and T. Y. Tsong, "Comparison of Kinetics of Formation of Helices and Hydrophobic Core during the Folding of Staphylococcal Nuclease from Acid", 1994, pp. 40–45.

C. M. Jones, E. R. Henry, et al., "Fast Events in Protein Folding Initiated by Nanosecond Laser Photolysis", 1993, pp. 11860–11864.

D. O. V. Alonso, K. A. Dill, et al., "The Three States of Globular Proteins: Acid Denaturation", 1991, pp. 1631–1649.

Jeanne Rudzki Small, "Deconvolution Analysis for Pulsed-Laser Photoacoustics", 1992, pp. 505–521.

Jeanne Rudzki Small, Louis J. Libertini, et al., "Analysis of photoacoustic waveforms using the nonlinear least squares method", 1992, pp. 29–48.

Cristiano Viappiani and Jeanne Rudzki Small, "Combined photoacoustic and fluorescent quenching studies on organic dyes", 1992, pp. 285–294.

Enoch W. Small, Louis J. Libertini, David W. Brown, and Jeanne Rudzki Small, "Optical studies of molecular motions: using fluorescence anisotropy decays to determine the shapes of dye molecules, proteins, and nucleosomes", 1991, pp. 345–356.

Jeanne Rudzki Small, Stephen H. Watkins, Barbara J. Marks and Enoch W. Small, "Analysis of photoacoustic waveforms using the Method of Moments", 1990, pp. 231–243.

Jeanne Rudzki Small and Shane L. Larson, "Photoacoustic determination of flourescent quantum yields of protein probes", 1990, pp. 126–136.

Enoch W. Small, Louis J. Libertini, David W. Brown, and Jeanne Rudzki Small, "Extensions of the Method of Moments for deconvolution of experimental data", 1989, pp. 36–53.

Jeanne Rudzki Small, Jonathon J. Hutchings and Enoch W. Small, "Determination of fluorescent quantum yields using pulsed-laser photoacoustic calorimetry", 1989, pp. 26–36.

Enoch W. Small, Louis J. Libertini and Jeanne Rudzki Small, "Molecular shapes from rotational diffusion: dye molecules, proteins and nucleosomes", 1988, pp. 97–107.

Jeanne E. Rudzki, Joshua L. Goodman, and Kevin S. Peters, "Simultaneous Determination of Photoreaction Dynamics and Energetics Using Pulsed, Time-Resolved Photoacoustic Calorimetry", 1985, pp. 7849–7854.

Jeanne E. Rudzki and Kevin S. Peters, "Picosecond Absorption Studies on Rhodopsin and Isorhodopsin in Detergent and Native Membrane", 1984, pp. 3843–3848.

Kevin S. Peters, Edward Pang, and Jeanne Rudzki, "Picosecond Dynamics of Hydride Transfer", 1982, pp. 5535–5537.

C. B. Anfinsen, "The Formation and Stablization of Protein Structure", 1972, pp. 737–749.

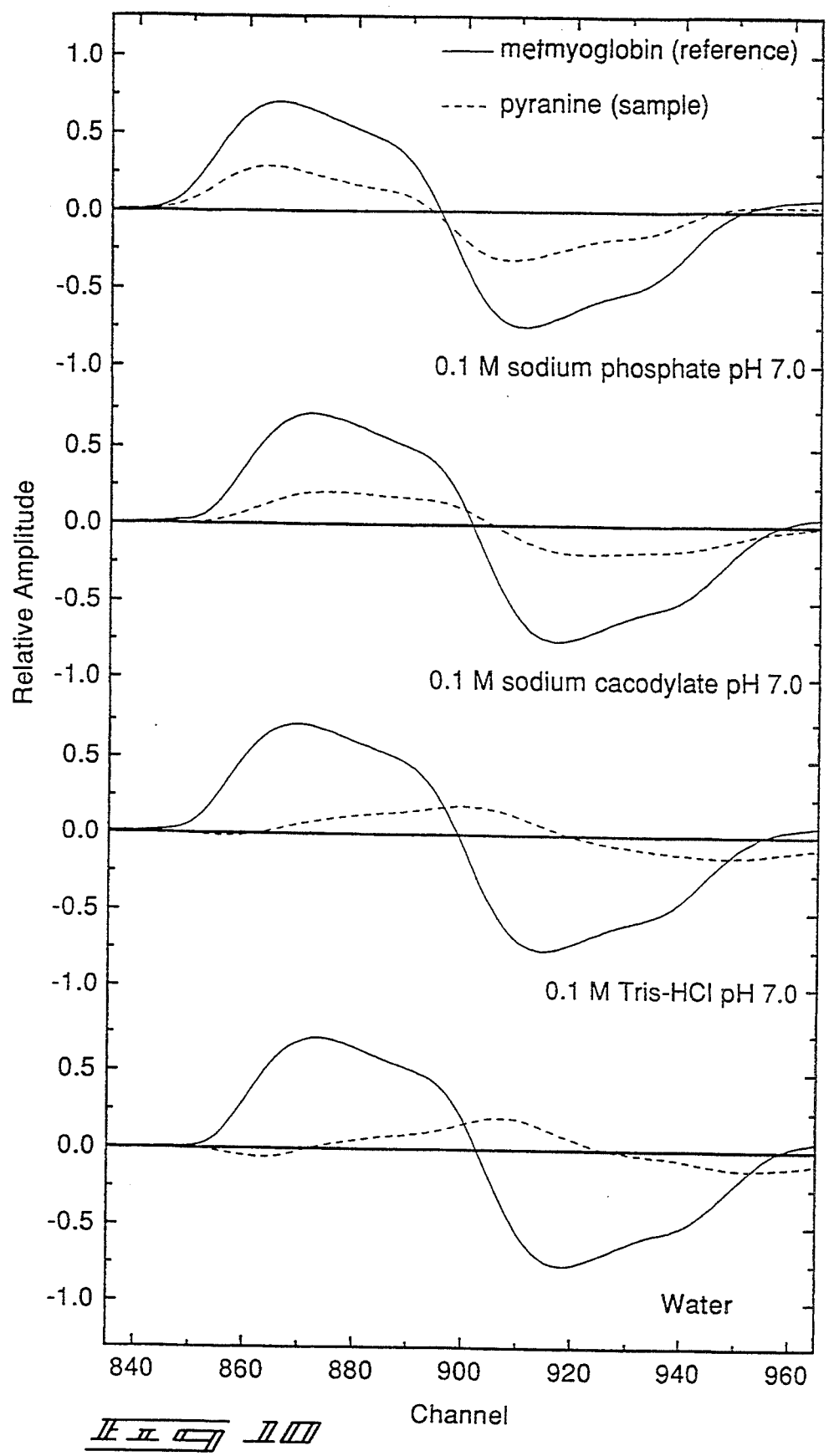

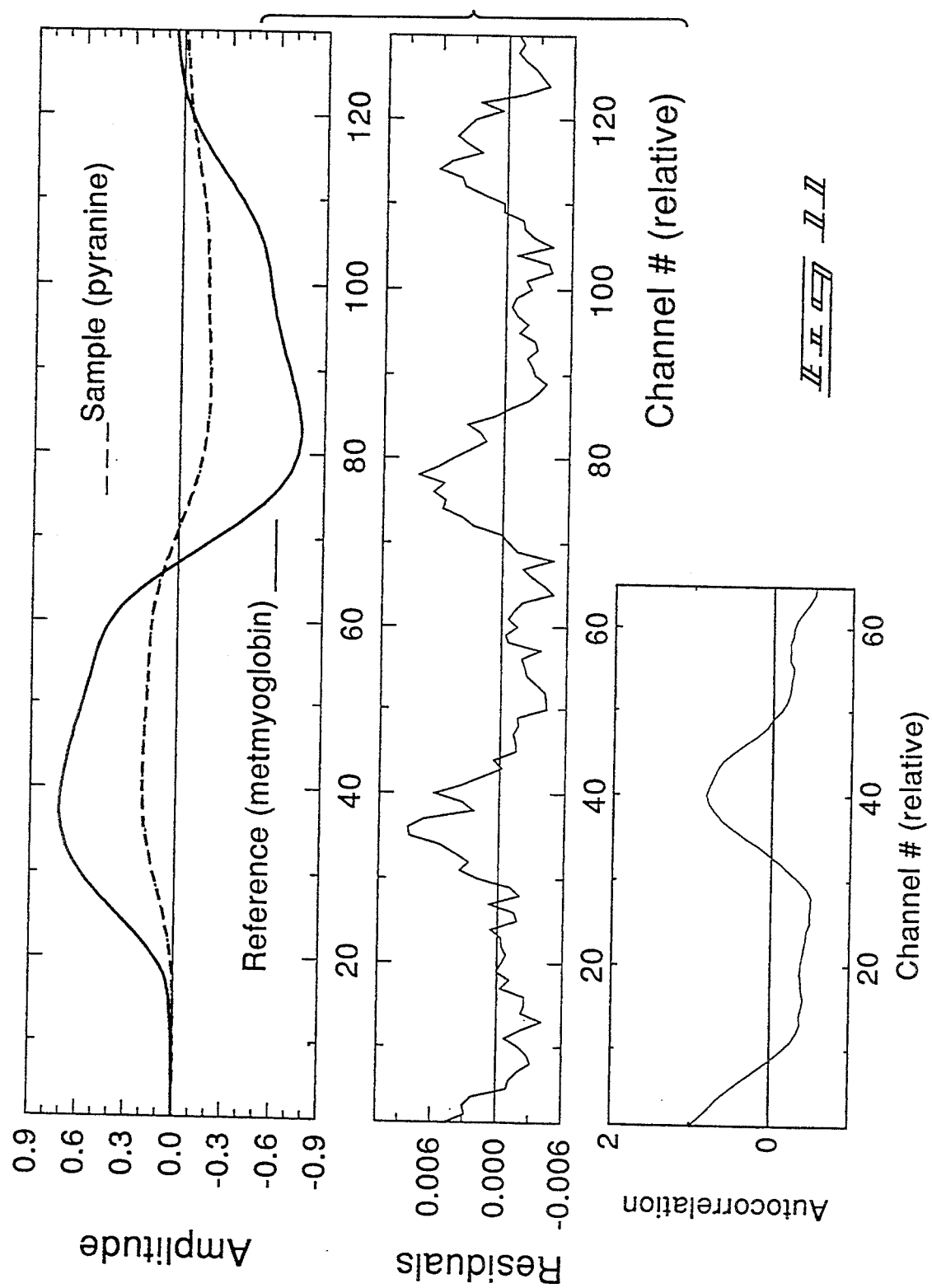

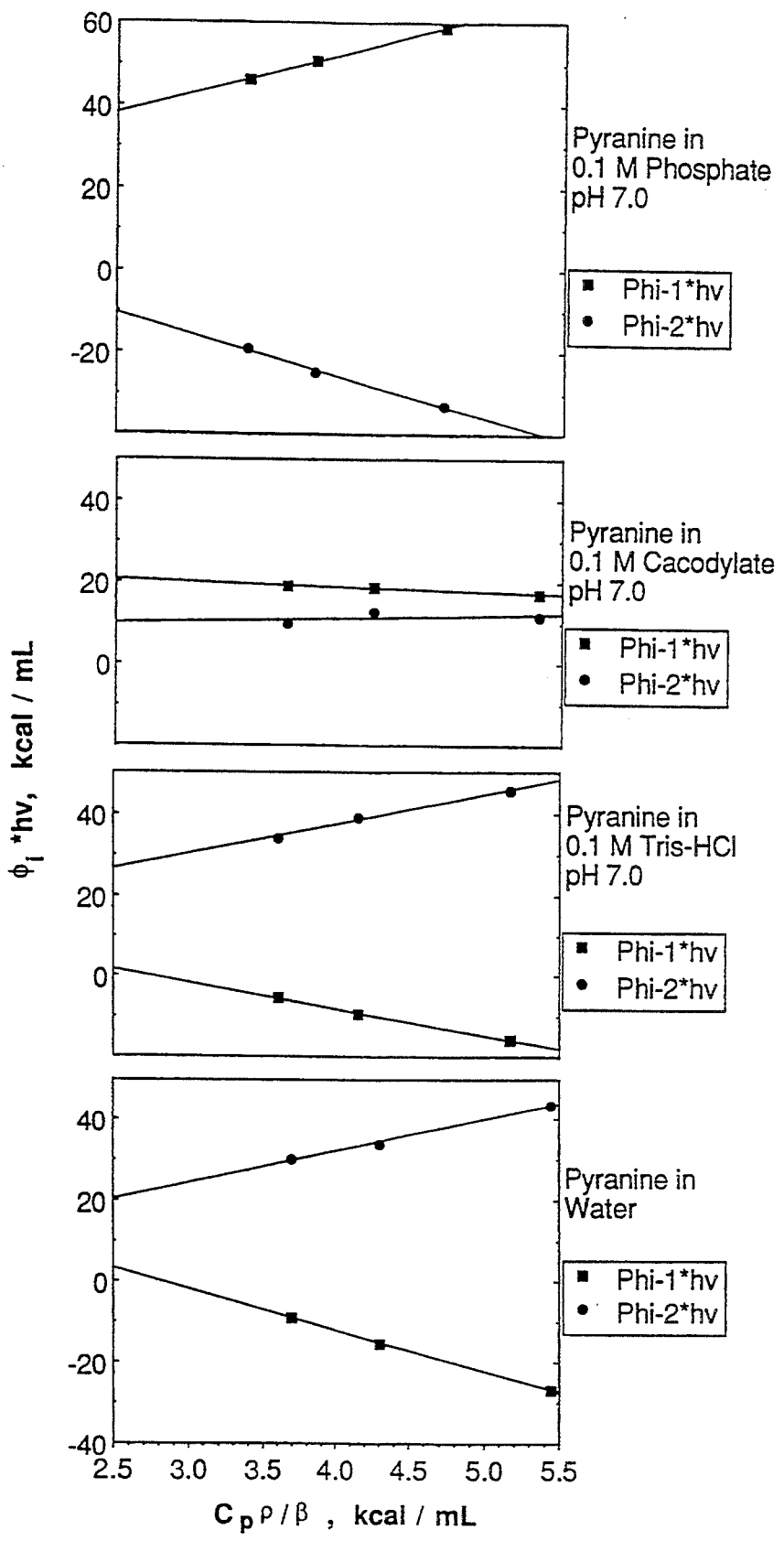

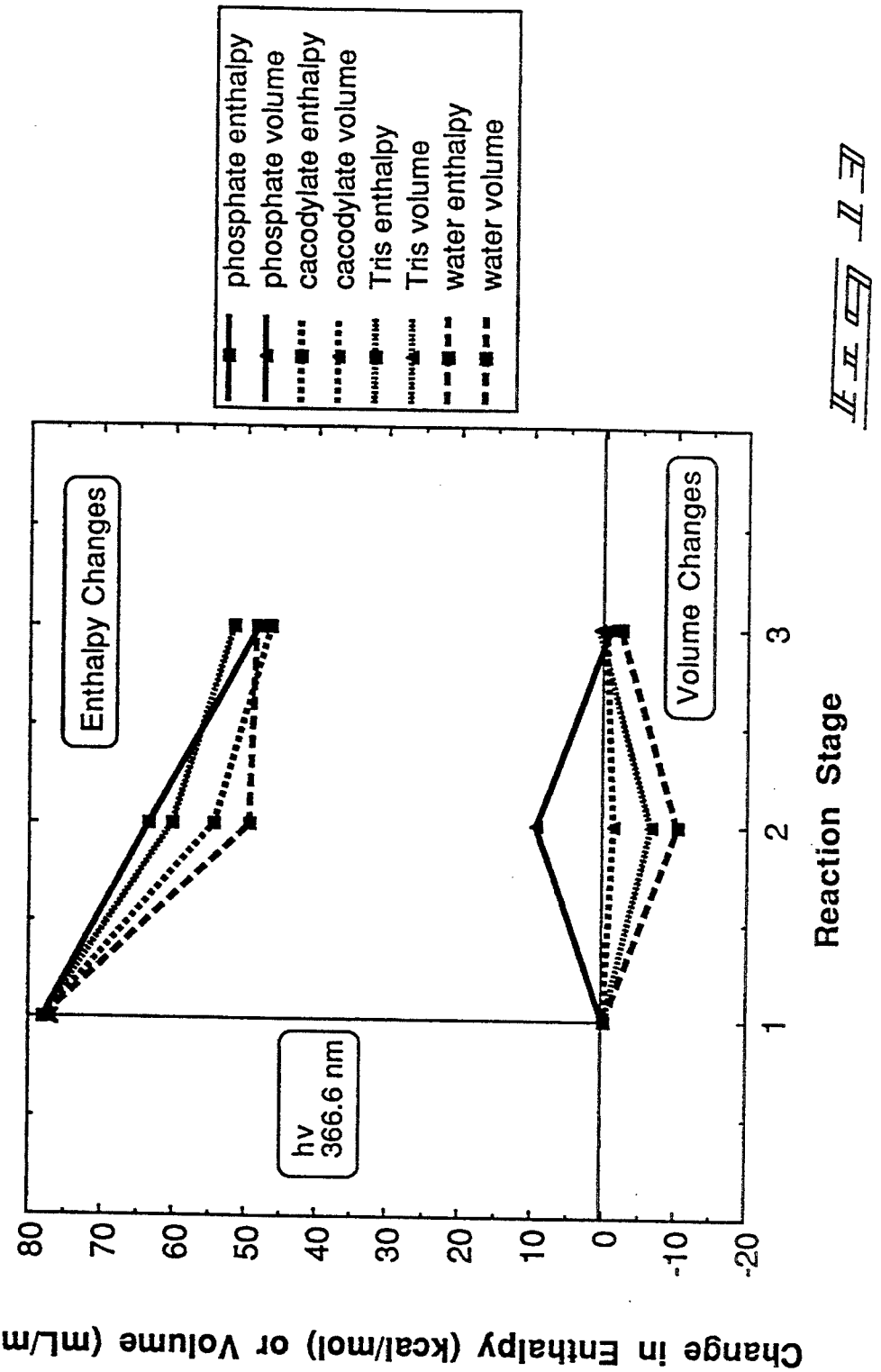

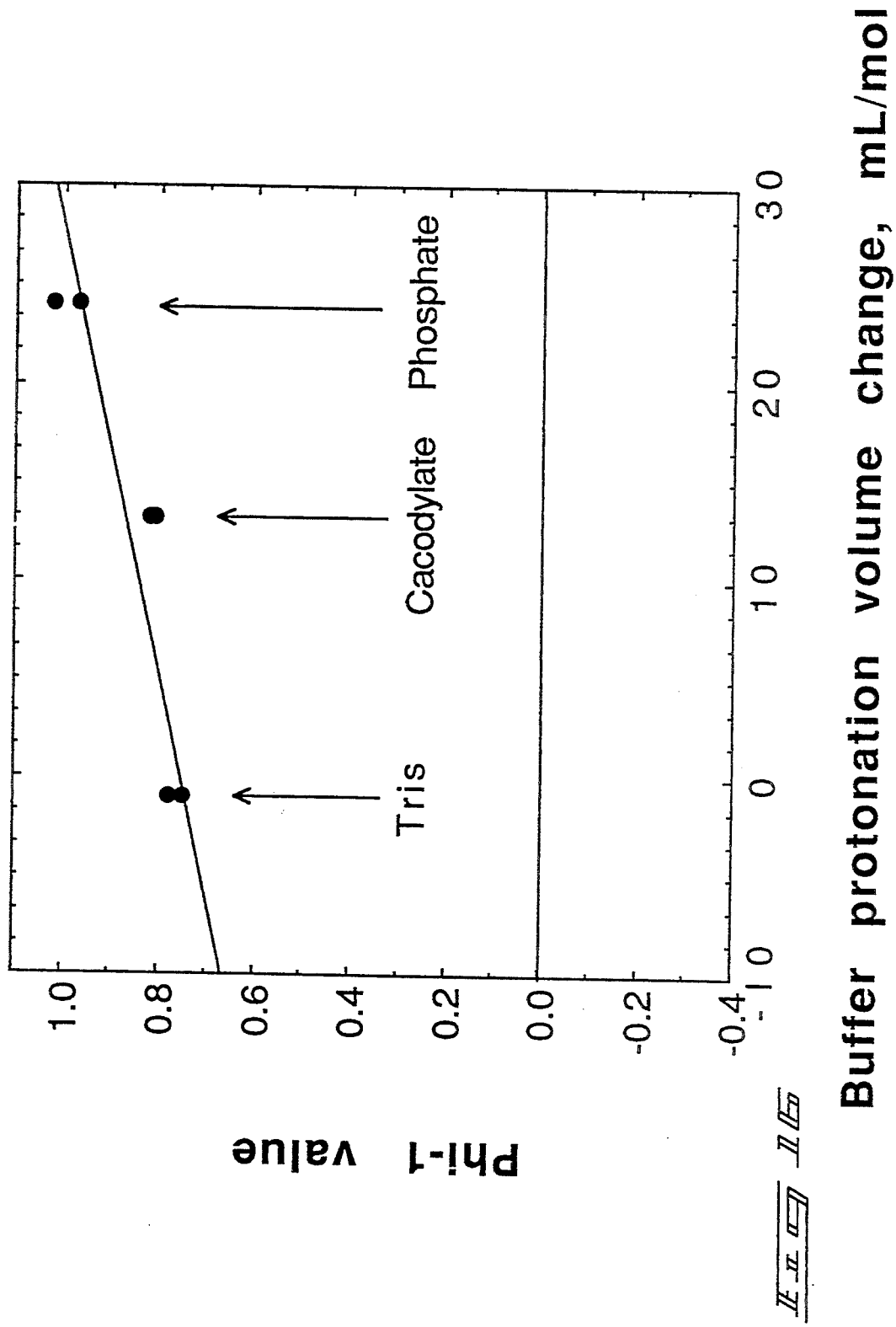

METHODS FOR PHOTOACOUSTICALLY ANALYZING CHEMICALS AND CHEMICAL REACTIONS USING PHOTOACTIVE PARTICLE-EMITTING COMPOUNDS

TECHNICAL FIELD

The field of this invention is methods for photoacoustically analyzing and characterizing chemicals and chemical reactions using photo-released protons and resultant acoustical effects.

BACKGROUND OF THE INVENTION

It has previously been recognized that molecules contained in a liquid sample can be stimulated using a suitable stimulating light source. Lasers are often used as the stimulating light source. Other electromagnetic beams may also be useful as stimulating beams. The stimulating beam is pulsed into the sample. The beam pulses cause volumetric changes in the sample which generate pressure waves. The resultant pressure waves are detected by a suitable acoustic transducer, such as a piezoelectric transducer. The transducer is acoustically coupled to the sample container to enhance detection of the pressure waves. The resulting pressure wave information has been used in analytical chemistry for characterizing one or more components of the sample. The technique of light stimulation and associated acoustical detection is more commonly known as photoacoustic analysis.

U.S. Pat. No. 4,303,343 describes a photoacoustic system which uses a laser light or other stimulating beam. The stimulating beam is presented in pulses of duration described therein to be $10^{-7}$ to $10^{-2}$ seconds. The beam pulses are directed upon a liquid or bulk solid sample having low absorbance of the stimulating beam. The frequency of the stimulating beam is varied to provide data used to define a characterizing curve indicating energy absorbance as a function of the stimulating beam frequency. This information is used in characterization of the sample compounds.

Despite the prior systems for photoacoustic analysis, there remains a need for improved photoacoustic analytical methods having the ability to resolve rapid molecular conformational changes. Molecular conformational changes are of general interest for a broad range of chemicals. They are of particular interest in the analysis of peptides, proteins, and other biological molecules for which current methods of analysis are of only limited usefulness.

There is also a need for improved methods for chemical analysis of reactions, reaction intermediates and reaction mechanics during very short periods of time after a chemical stimulus has occurred. Prior art analytical systems provide "stop-action" analysis for chemical reactions by rapidly mixing two solutions in about 1 millisecond. The resulting mixture is monitored using absorbance or fluorescence detection methods.

Alternatively, it is possible to use calorimetric analytical methods to better understand chemical reaction processes. Calorimetric analytical techniques are employed due to the importance of energy relationships between reactants and products. The energy change associated with reactions are thus measurable using calorimetric techniques. For extremely fast reactions, it is sometimes difficult to measure enthalpic changes. The reactions must either be slowed by cooling, or fast calorimetric methodologies must be used.

Such systems do not allow resolution of the reaction process when there are very rapid transformation periods on the order of $10^{-10}$ to $10^{-8}$ seconds. Rapid transformation capability is sought so that the equivalent of stop action or freeze frame data can be obtained during periods of chemical degradation, reaction between two distinct reactants, molecular conformational changes, and other similar transformations herein referred to as reactions.

Molecular conformational changes of many molecules are believed occur within a time range of $10^{-10}$ to $10^{-5}$ seconds after a chemical stimulus for change has been presented. Prior techniques have not been effective at obtaining information which can be used to provide freeze frame information concerning the processes involved in conformational changes, such as in conformational changes demonstrated in biological molecules.

BRIEF DESCRIPTION OF THE DRAWINGS

Preferred embodiments of the invention are described below with reference to the accompanying drawings, which are briefly described below.

FIGS. 9–16 are graphs showing data which relates to the examples described below.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
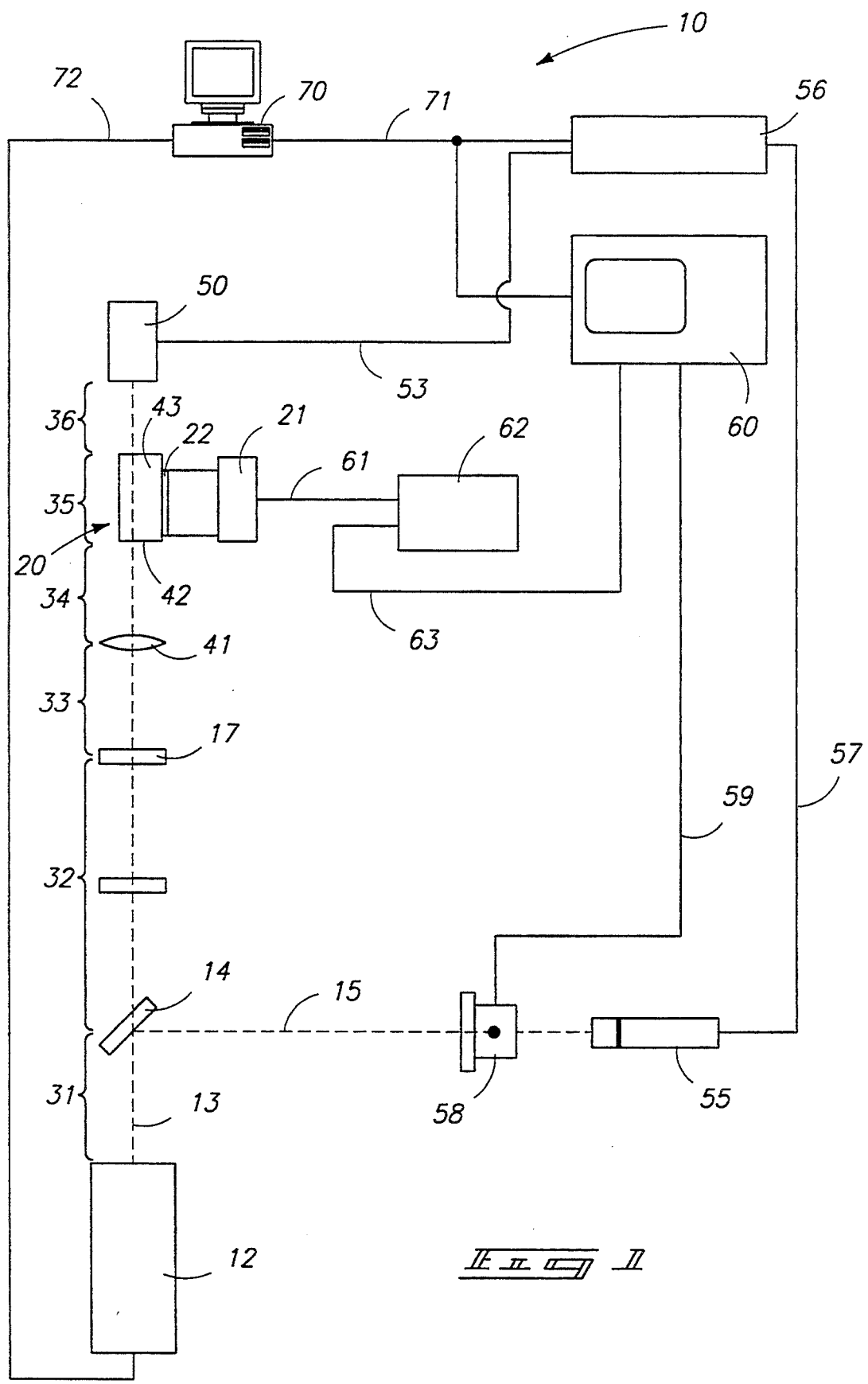
FIG. 1 is a schematic view showing an analytical system used in performing the methods of this invention.

FIG. 1 shows a photoacoustic analyzer system 10 used to conduct the methods described herein. Photoacoustic analyzer 10 includes a suitable electromagnetic beam source 12 which is advantageously in the form of a nitrogen-pumped dye laser. Laser 12 is configured to produce stimulating electromagnetic beam pulses. The stimulating electromagnetic beam pulses are advantageously in the near ultraviolet light range, preferably with wavelengths in the range of approximately 250 to approximately 400 nanometers, even more preferably in the range of approximately 300 to 380 nanometers. Alternative wavelength beam sources may also be useful in the inventions described herein.

The beam pulses from beam source 12 have time durations called stimulation pulse periods. The stimulating pulse periods are preferably less than $10^{-7}$ seconds (100 nanoseconds). More preferably, the stimulation pulse periods are in the range of approximately $10^{-10}$ to $10^{-7}$ seconds.

Figure 2:
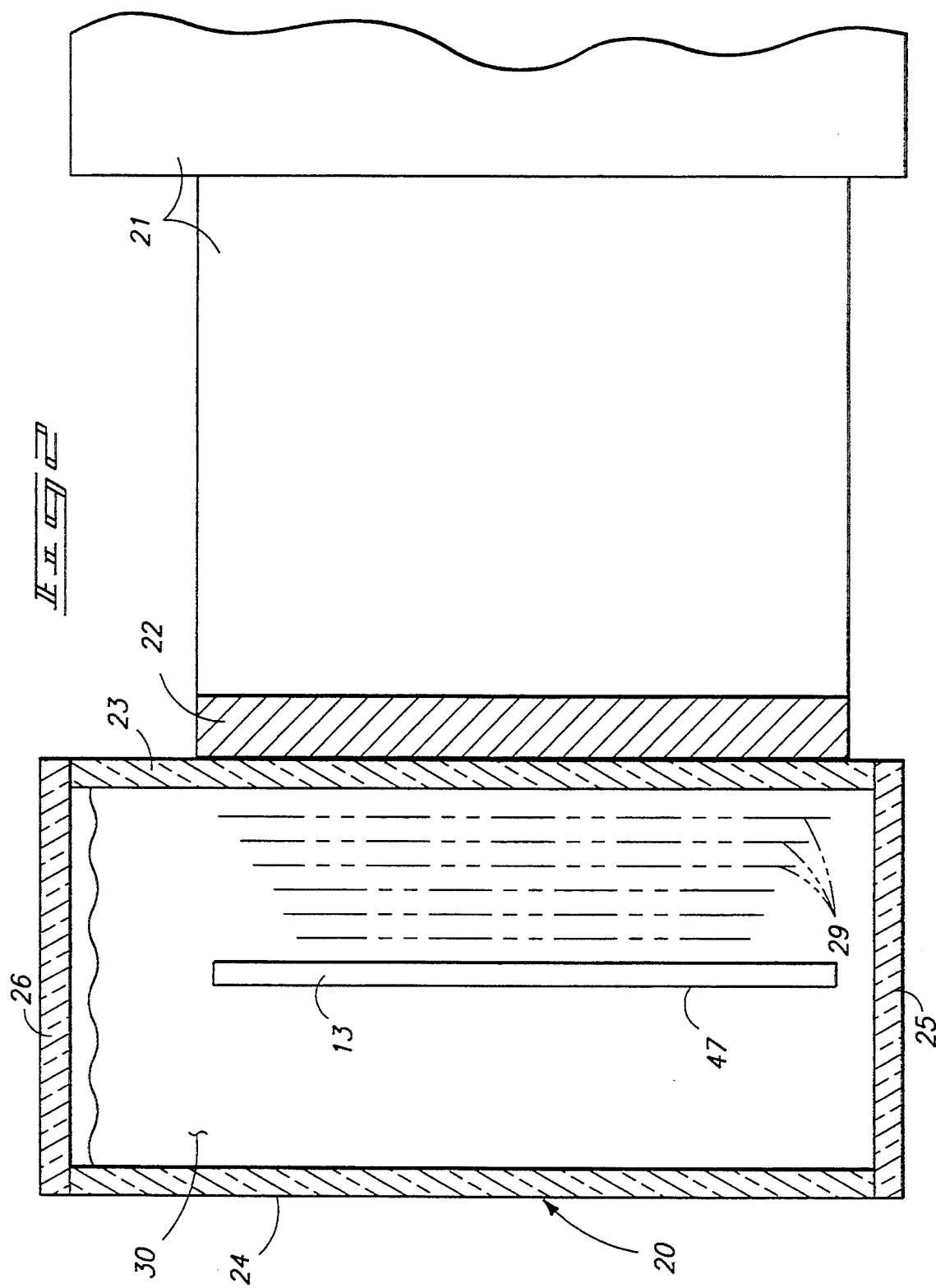
FIG. 2 is a sectional view showing a sample cuvette with sample liquid therein.

The laser beam 13 emitted from laser 12 is beamed into a sample cuvette 20. FIG. 2 shows an enlarged view of the sample cuvette 20. Cuvette 20 is preferably rectangular having a height of 2 centimeters, a width of 1 centimeter, and depth of 1 centimeter. The cuvette has opposing first and second side walls 23 and 24. Cuvette 20 also has a bottom wall 25 and top wall or removable cap 26. Cuvette 20 also has a front wall 42 and a rear wall 43. The walls of cuvette 20 are most preferably transparent or substantially transparent to the wavelength of the stimulating beam emitted from laser 12.

First side wall 23 is proximate to an acoustic transducer 21. Transducer 21 is advantageously a piezoelectric ultrasonic transducer having a relatively high nominal frequency, for example approximately 1 megahertz. An exemplary acoustic transducer is a Panametrics brand model V103 or many other suitable types. The sample cuvette is acoustically coupled to acoustic transducer 21 using a suitable acoustic coupling 22. As shown acoustic coupling 22 is a layer of suitable commercially available silicone grease.

Transducer 21 senses acoustic or pressure waves 29 which are generated in a liquid sample 30 held within the interior of sample cuvette 20. Pressure waves 29 are communicated through sample liquid 30, sidewall 23 and acoustic coupling 22 to reach acoustic transducer 21. Pressure waves 29 are caused by processes occurring within liquid sample 30 as stimulated by the beam from laser 12. The pressure waves are manifestations of volumetric changes occurring within the sample. These volumetric, changes are described in greater detail below.

FIG. 1 shows that the laser beam 13 emits from laser 12. Beam 13 advantageously traversed along a beam path which is for purposes of illustration and explanation divided into beam path segments 31–36 which are explained more fully below.

Beam 13 is directed against a beam splitter 14. Beam splitter 14 divides the laser beam and produces a reflected beam 15 which is directed laterally from the path of main beam 13. The first beam path segment 31 is defined between laser source 12 and beam splitter 14. A second beam path segment 32 extends from beam splitter 14 to a beam shaper 17. Beam 13 has a reduced power along second path segment 32 as compared to along first path segment 31.

Stimulating beam 13 is also directed through a suitable beam shaper, such as the beam shaper 17 shown. An optional variable filter 16 can be used to allow beam power to be adjusted. Beam shaper 17 is advantageously a non-transparent piece having a rectangular slit formed therethrough. Beam 13 is partially blocked by the beam shaper and emits therefrom with an elongated rectangular cross-sectional beam shape as illustrated in FIG. 2. The beam passing from beam shaper 17 traverses a third beam path section 33. The end of third beam path section 33 is defined by a imaging element or elements 41. The imaging element is advantageously in the form of a cylindrical focusing lens which is aligned with the longitudinal axis of the elongated rectangular beam shape. This construction allows the beam to be focused onto the sample 30 held in cuvette 20. The fourth beam path section 34 extends from the focusing lens 41 to the cuvette. The focused beam is directed through front wall 42 of cuvette 20.

The beam pattern or cross-sectional beam shape 47 shown in FIG. 2 defines an illuminated sample portion or volume extending between the interior surfaces of front and back walls 42 and 43. This illuminated volume is the portion of the sample which is stimulated by the beam. In a preferred arrangement the beam pattern 47 is 11 millimeters high and typically between 0.2 to 0.5 millimeter wide. This extends over an interior depth of approximately 0.9–1 centimeter between walls 42 and 43. An exemplary sample illuminated volume would thus be approximately 40–50 microliters. The fifth beam path segment 35 is defined by the traversal through cuvette 20.

The stimulating beam 13 traverses the cuvette and emits through the back wall 43. The resulting output beam traverses along a sixth beam path segment 36 and is directed upon an output beam sensor 50 which senses and measures the power of the beam or energy content of the output beam pulse which is used in analysis as explained below. Conductors 53 are connected between output beam sensor 50 and an energy meter 56 to communicate an output beam signal which is indicative of the energy of the beam pulses output from the sample. This serves to provide a beam pulse output energy measure used in the analyses described below. The energy meter 56 is connected to a computer 70 which serves as a central controller, data storage and analytical computer. A general purpose interface bus 88 is advantageously used as an electrical data conductor between energy meter 56 and computer 70.

FIG. 1 shows the reflected beam 15 is directed upon input beam detector 55. The input beam sensor 55 is electrically coupled to an associated energy meter 56 using conductors 57 to form a subsystem for measuring beam power or energy content of the pulses of reflected beam 15. Energy meter 56 advantageously has two inputs allowing signals from both sensors 50 and 55 to be input and converted to energy measurement data which is communicated on the data bus 88 to computer 70. The energy of the reflected beam pulses are proportional to the energy of the pulses emitted from laser 13. Thus they are indicative of the energy of the stimulating beam pulses received by sample 30 after calibration. Computer 70 is also connected to receive a beam pulse input energy signal via data bus 88 from energy meter 56 which is a measure indicative of the energy of the stimulating electromagnetic beam pulse beamed into the liquid sample 30.

The reflected beam 15 is also directed so as to activate a beam trigger 58. Beam trigger provides a trigger signal which is communicated over conductors 59. Beam trigger 58 is used to trigger data acquisition by a recording digital oscilloscope 60, such as a Tektronix model 2430. Oscilloscope 60 stores data points at a suitable frequency or time spacing, such as preferred rate of every 10 nanoseconds. The readings are stored during an acoustic response detection period which advantageously starts at the end of the stimulating beam pulse and continues for approximately 10 microseconds.

Transducer 21 is connected to provide a transducer electronic output signal which is communicated over conductors 61 to a closed positioned transducer preamplifier 62. The amplified signal from preamplifier 62 is communicated by conductors 63 to oscilloscope 60. Oscilloscope 60 is connected to the data bus 88 to provide data to computer 70.

The analytical system 10 further preferably includes a central controller 70, such as a suitably configured computer (personal computer) or other controller. Controller 70 is connected by conductors 71 to receive data from oscilloscope 60. Controller 70 is also connected by conductors 72 to the beam source 12 to provide an activating control signal which provides the pulsed beam 13.

Methods

Analyzer 10 is advantageously used in the performance novel methods according to this invention. The novel methods preferably include preparing a liquid sample, such as sample 30. The liquid sample includes a solvent and one or more chemical species of interest for analysis. A variety of solvents are suitable dependent upon the chemical system of the sample. Preferred solvents include water and suitable alcohols. Other protic solvents are believed to in general be useful in these methods. Additionally, it is possible to use co-solvents combining such known workable solvents as water, methanol, ethanol, isopropanol, and others with an even wider variety of solvents. The preferred protic solvents can be used in even very low concentrations, for example 1% by weight, and the desired positive effects with regard to freed proton mobility within the sample will produce operable readings. Nonetheless, the solvent or multi-solvent system selected will depend upon the particular chemical system being analyzed.

The chemical species of interest for analysis using the novel methods can include a wide variety of compounds including molecular and ionic species. Biological molecules and reactions between biological molecules and other reactants are of particular interest because of the improved analytical capabilities of the novel methods for such applications. However, the analytical techniques of this invention are equally applicable to many other chemical species and reactions.

The methods of this invention further include selecting a suitable photoactive particle-emitting compound. The photoactive particle-emitting compound is more preferably selected to be a photoactive charged particle-emitting compound, even more preferably a photoactive proton-emitting compound. It is possible to select photoactive proton-emitting or other particle-emitting compounds which are photolabile or nonphotolabile. Suitable photolabile compounds can be selected which provide both proton emission and two resulting groups. The resulting groups are divided from the photolabile compounds upon photolysis by action of a stimulating electromagnetic beam. The resulting groups divided from the proton-emitting compound can be either reactive or nonreactive with the chemical species of interest. Alternatively, a resulting group from a photolabile proton emitter can include at least one chemical species which is of interest for analysis.

The photoactive proton-emitting compounds used in the novel methods of this invention are molecular or ionic compounds comprising a chromophoric group of atoms and bonds and a remaining or secondary group of atoms and bonds. The photoactive proton-emitting compounds used in this invention are capable of very rapid release of one or more protons ($H^+$) or relatively small groups having a reactive proton or protons attached thereto. The protons are released due to photoactivation by a stimulating electromagnetic beam, for example a laser beam, flash lamp beam, or other stimulating beam having a wavelength which is appropriate for activating the chromophore group. The released proton can emanate from a hydrogen atom which is present before stimulation in either the chromophore group of atoms and bonds, or in the second or remaining group of atoms and bonds. The proton or other particle is released within a proton or particle release time period which is less than 100 nanoseconds ($10^{-7}$ seconds), more preferably less than approximately 10 nanoseconds ($10^{-8}$ seconds), for photoactive proton-emitting compounds as defined in this invention.

The chromophoric group absorbs light or other suitable stimulating electromagnetic radiation within a chromophore stimulation bandwidth having associated stimulation frequencies or wavelengths which provide photoactivation and release of the proton species from the particular photoactive proton-emitting compound.

The second or remaining group of atom and bonds forming a part of the proton-emitting compound can vary widely. Second groups can be selected from essentially any chemical group which can be bonded to a chromophoric group. The second group can be a molecular or ionic group which when divided from the chromophoric group becomes a molecule of interest for analysis. Alternatively, the second group can merely be a group associated with a chromophore containing compound which has desired properties for use in a sample mixture also containing one or more distinct and separate chemical species of interest in the analysis being conducted.

The proton-emitting compound can be either photolabile or nonphotolabile. A photolabile proton emitter is one which is irreversibly structurally altered in the course of it response to photons or other stimulating photolytic radiation. One aspect of the structural alteration is the separation of the proton species from the remaining portions of the original atoms of the proton-emitting compound. For purposes of this invention and the claims contained herein, "irreversibly" must be interpreted to mean substantially irreversible within a time frame relevant to the acoustic measurement period. The acoustic measurement period is the period after stimulation during which data is taken indicating the response of the sample to proton release. Subsequent reversal of the proton emission reaction after acoustic sensing has been completed are currently understood to typically not affect the methods of this invention.

Examples of photolabile proton-emitting compounds applicable to the methods of this invention include: 2-hydroxyphenyl 2-nitrophenylethyl phosphate, sodium salt; adenosine-5'-triphosphate, 3—O—(1-(-2-nitrophenyl)ethyl) ester, disodium salt; 1-(2-nitrophenyl)ethyl phosphate; 3',5'-dimethoxybenzoin phosphate; and fluorescein-bis-4,5-dimethoxy-2-nitrobenzyl ether.

Figure 3:
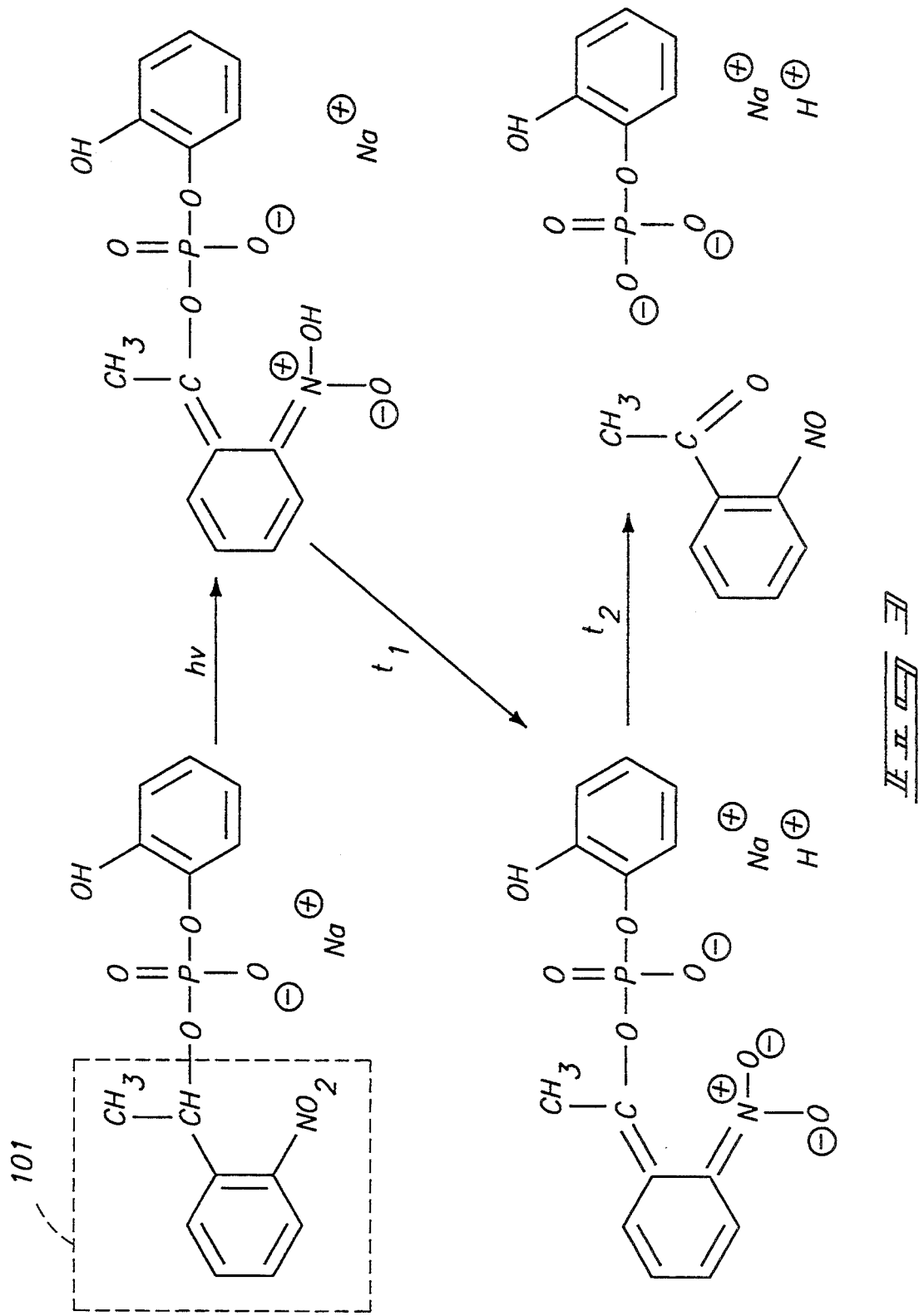
FIG. 3 is a molecular reaction diagram showing a process relevant to the invention.

FIGS. 3–7 show additional molecular diagrams which illustrate chromophoric groups which can be bonded to a second group to provide proton-emitting compounds which are expected to be useful in the methods of this invention. FIG. 3 has a box 101 showing the chromophoric group which in this case is a 2-nitrophenyl ethyl chromophoric group. Attached to the chromophoric group is the second group which is a 2-hydroxyphenyl phosphate group.

Figure 4:
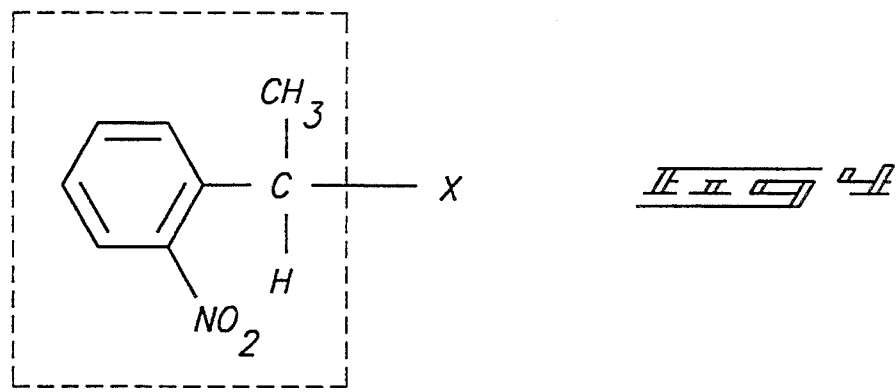
FIGS. 4–7 are molecular diagrams demonstrating alternative chromophoretic groups believed useful in the inventive methods.

FIG. 4 shows the chromophoric group of box 101 coupled to an undefined second group generically identified as "X".

Figure 5:
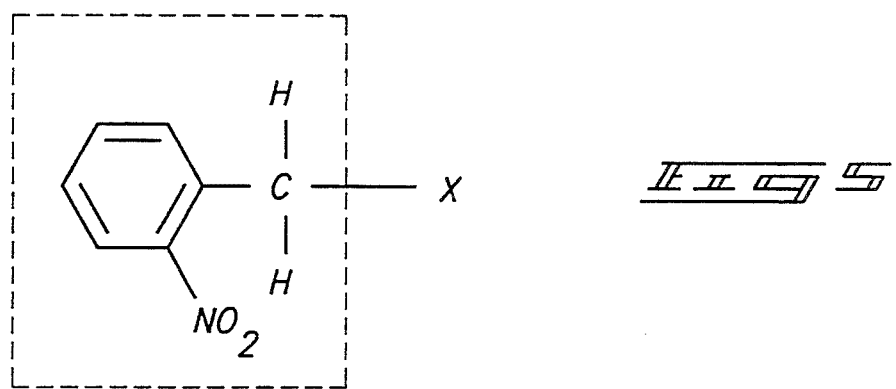

FIG. 5 shows another chromophoric group also coupled to an undefined second group "X". The chromophoric group of FIG. 5 is also believed to be appropriate in preparing proton-emitting compounds used in this invention. The chromophoric group of FIG. 5 is termed a 2-nitrobenzyl group.

Figure 6:
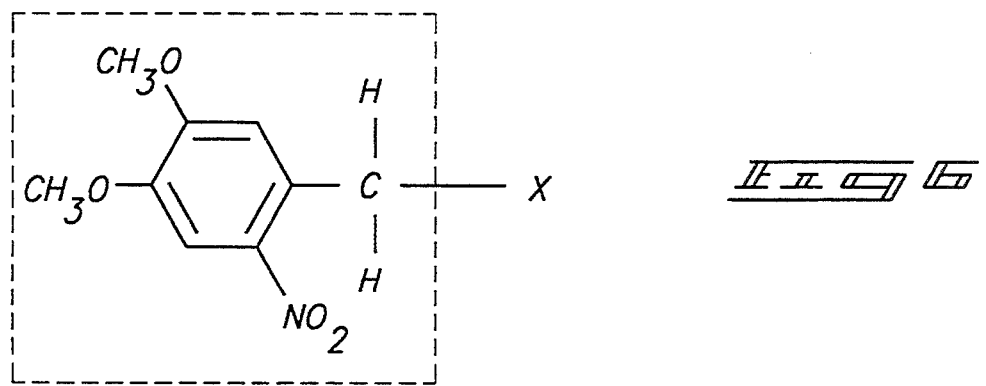

FIG. 6 shows a further chromophoric group also coupled to an undefined second group "X". The chromophoric group of FIG. 6 is also believed to be appropriate in preparing proton-emitting compounds used in this invention. The chromophoric group of FIG. 6 is termed a 4,5-dimethoxy-2-nitrobenzyl group.

Figure 7:
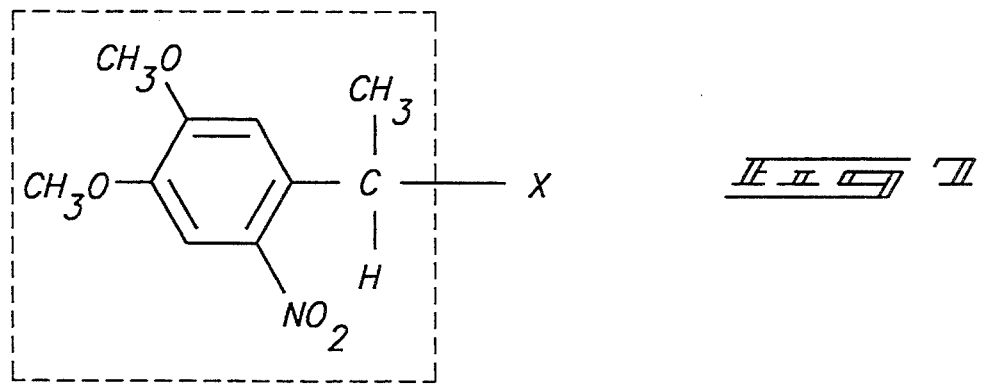

FIG. 7 shows a further chromophoric group also coupled to an undefined second group "X". The chromophoric group of FIG. 7 is also believed to be appropriate in preparing proton-emitting compounds used in this invention. The chromophoric group of FIG. 7 is termed a 4,5-dimethoxy-2-nitrophenyl ethyl group.

Additional photolabile compounds believed suitable for use in the methods of this invention are described in the following patents or publications which are hereby incorporated by reference: a) PCT Application No. PCT/GB91/01941 which is International Publication No. WO92/08720, entitled Photo-Labile Compounds, Their Synthesis and Use as Fluorophores; b) European Patent Application No. 87309271.4 which was published as European Patent Specification Publication No. EP0233403B1, entitled Photo-labile Protecting Agents and Method.

A nonphotolabile proton-emitting compound is transiently altered by a stimulating electromagnetic beam to produce an excited electronic state therein. This excited electronic state of the proton emitter causes the binding affinity for one or more protons thereon to become sufficiently low that the proton is emitted into a free state and can be called a freed proton. Typically the excited electronic state will dissipate in a relatively short period of time, such as within less than 10–100 nanoseconds after stimulation. Thereafter the freed proton reassociates with the remaining portions of the nonphotolabile proton-emitting compound. However, in the photoactive proton emitting compounds useful for and to be interpreted as defined in the methods of this invention, this reassociation is sufficiently delayed that it is substantially not within the acoustic measurement period. Alternatively, it is also possible to use compounds which have protons which reassociate within the acoustic measurement period, but for which the reassociated process can be clearly identified as a separate event when analyzing the acoustic output data.

Examples of nonphotolabile proton-emitting compounds believed useful in the methods of this invention include a variety of molecular or ionic compounds having a hydroxyl group (—OH) such that the electronic excited state affinity $pK_a$ (affinity for $H^+$) of the hydroxyl hydrogen is substantially less than the corresponding ground excited state affinity $pK_a$ associated therewith when the compound is not excited.

One class of compounds containing suitable nonphotolabile proton-emitting compounds is a class of compounds commonly known as the aromatic alcohols. Such class includes molecules having one or more benzene rings and one or more hydroxyl or equivalent alcohol functional groups contained therein.

Another example of a suitable nonphotolabile proton-emitting compound useful in this invention is pyranine (8-hydroxypyrene-1,3,6-trisulfonic acid, trisodium salt). This proton emitter is described in an example given below. Other possible nonphotolabile proton emitters include: phenol; 4-chlorophenol; 1-naphthol; 2-naphthol; tyrosine; naphthofluorescein; fluorescein; 7-hydroxycourmarin.

The methods of this invention are also believed to be operable with non-proton particles having high mobility when photoexcited and divided from a compound contained in sample solutions, such as described herein. The photoexcited particles are preferably relatively small, limited to a relatively small number of atoms and bonds. These atoms and bonds are grouped together and can be photoactivated to divide from remaining portions of the particle-emitting compounds in a manner similar to the proton-emitting compounds discussed herein. The particle-emitting compounds are most preferably charged-particle-emitting compounds. For example, the proton is a positively charged particle and is emitted from a positively-charged particle-emitting compounds as explained above. In an analogous fashion a hydroxide ion ($OH^-$) is relatively small and is a negatively-charged particle which can be photoactivated to emit from a negatively-charged particle-emitting compound.

Non-proton particle-emitting compounds believed useful in methods of this invention include various hydroxide-ion-emitting compounds which can be synthesized with a chromophoric group and an associated secondary group as explained above. One such hydroxide emitter is believed to be sulfontated 4,4'-bis(dimethylamino)triphenylmethane leucohydroxide. This compound absorbs radiation having wavelengths in the region of 280 nanometers to 410 nanometers. It releases a single hydroxide group rapidly in high quantum yield. Release in approximately 40 nanoseconds is believed to occur. The methodology described herein is applicable to such negatively charged hydroxide emitting compounds in an fashion analogous to the proton emitters described above.

The methods further include providing the photoactive proton-emitting or other particle-emitting compound in the liquid sample. This is advantageously accomplished by mixing a suitable amount of the photoactive proton-emitting compound into the sample solvent. This can be done either before or after the mixing of any additional chemical species of interest for analysis. The providing step is advantageously accomplished so as to provide a desired concentration of photoactive proton-emitting compound or to achieve a desired optical absorbance level appropriate for balanced energy absorption by the sample.

The concentration of proton or other particle emitter will vary dependent upon the analytical application for which it is being used. In general sufficient proton emitter is used to yield and supply a released or freed proton concentration as desired for the testing being conducted. This can range widely. More typically, the desired concentrations of photoactive proton-emitting compound are in the range of approximately 1 micromolar to approximately 100 millimolar, more preferably in the range of approximately 10 micromolar to approximately 10 millimolar, even more preferably in the range of approximately 100 micromolar to approximately 1 millimolar.

It is also a significant parameter that the photoactive proton-emitter be added in sufficient quantities that the demonstrated absorbance of the liquid sample is appropriate for generating usable data. Operation of the methods is advantageously in the range of 0.2 or greater optical absorbance. However, if the absorbance of the sample is very high then the stimulating beam is dissipated principally over a short distance from the front wall of the cuvette. This results in relatively non-uniform energy release and most of the acoustic wave energy propagates from near the front wall of the cuvette. It is more preferred that the absorbance is chosen to provide more uniform energy absorbance through the sample between the front and back walls of the cuvette. This provides a relatively even energy level and the generation of approximately planar acoustic wave fronts which are directed against the face of the acoustic transducer. Thus preferred optical absorbance levels for the samples used in this invention are in the range of approximately 0.5 to approximately 2, even more preferably in the range of approximately 0.8 to approximately 1.1.

It should be further appreciated that in many instances the quantities of proton-emitting compound or compounds used is more appropriately governed by the absorbance parameter than other considerations.

The novel methods of this invention also include beaming a stimulating electromagnetic beam onto a liquid sample, such as liquid sample 30. The stimulating beam is preferably presented in a brief pulse. The pulse has a suitable duration which is herein described as a stimulation pulse period of time. Preferred pulse durations are in the range of approximately $10^{-10}$ to $10^{-7}$ seconds (100 picoseconds to 100 nanoseconds). The beam pulse durations are necessarily affected by the sample requirements and can vary according to parameters which are not fully understood at this time.

The beaming step is performed using a beam source which generates electromagnetic radiation of the desired type and frequency or wavelength. The stimulating radiation used will in general be governed by the radiation needed to stimulate the chromophoric group of the proton-emitting compound. The variety of chromophoric groups which can be used thus has an associated variety of suitable stimulating beam parameters. More preferably, the stimulating beam is in the near ultraviolet light range. Ultraviolet light in the wavelength range of approximately 250 nanometers to approximately 400 nanometers are more preferred with regard to many of the suitable proton-emitting compounds now recognized. Even more preferably the stimulating beam is light in the wavelength range of approximately 300 nanometers to approximately 380 nanometers.

The beaming step is performed using a beam having a suitable beam power to provide a desired beam pulse with suitable beam energy content. The power level of the stimulating beam and energy content of the stimulating beam pulse will necessarily vary significantly in accordance with the energy requirements of the sample system being tested. Such energy requirements will be affected by the proton-emitting compound selected and other sample constituents. It may further be affected by other parameters of the system, such as the temperature and pressure at which the sample is stimulated. Further the absorbance of the sample and the size of the illuminated sample volume will necessarily affect the power and beam pulse energy content requirements of the beaming step described for the novel methods of this invention.

Despite the potential variations in beam power and beam pulse energy content, some exemplary power and energy values will be given. Stimulating beam pulse energies ranging from approximately $10^{-1}$ to approximately $10^1$ microjoules per microliter of illuminated sample volume are typical. These correspond to stimulating beam incident power levels ranging from approximately 10 watts to approximately 1000 watts per microliter of illuminated sample volume for stimulation pulse periods of $10^{-8}$ seconds. Instantaneous power levels may vary during the stimulation pulse period leading to even higher instantaneous power peak values.

The beaming step is advantageously performing using a beam source which generates a laser or coherent beam. Such coherent beams are relatively better than other beams from noncoherent typical beam sources due to superior controllability and measurement ease and accuracy. Other beam sources are alternatively possible, for example flash lamps and other sources known for the particular type of stimulating beam to be used.

The stimulating beam is preferably beamed to the sample in a form having an elongated cross-sectional beam shape or pattern. The elongated beam pattern shape is more preferably defined by opposing side segments which are substantially parallel and relatively closely spaced compared to the longitudinal length of the elongated beam pattern. This configuration produces illuminated sample volume having parallel side faces. The parallel side faces generate acoustic wave fronts which can more effectively be measured by the acoustic transducer.

The preferred methods thus further include generating acoustic wave fronts from a substantially planar side face or faces of a planar illuminated sample volume by beaming a stimulating beam having an elongated beam pattern with substantially linear beam pattern side perimeter lines. The generating step is more preferably done using a stimulating beam having an elongated beam pattern with substantially parallel linear beam pattern side perimeter lines.

The wave front generating step described above is preferably done within a sample cavity defined within the cuvette. The sample cavity preferably has spaced sidewalls which are approximately parallel relative to one another. The beaming step described above is preferably done so as to orient the side faces of the illuminated sample volume in substantially parallel relationship to the sample cavity sidewalls and transducer sensing face.

The methods of this invention further include generating released protons or other particle species from the sample liquid. This generating step is accomplished by beaming the proton-emitting compound or compounds contained as a sample constituent. The beaming and resulting proton generating steps can be represented by an illustrative reaction shown diagrammatically in FIG. 3.

FIG. 3 is a molecular reaction diagram illustrating proton emission from and the photolysis of the molecule 2-hydroxyphenyl 2-nitrophenylethyl phosphate, sodium salt. The original molecule is shown at the top left position. In reaction 1 the original molecule absorbs a photon of light (hν) and experiences a very fast rearrangement which includes an intramolecular proton transfer within a few picoseconds. In the next phase, reaction 2, the proton is actually released from the molecule shown in the top right position. This proton release and associated reaction mechanics cause a transformation to the molecule shown in the lower left. This transformation associated with reaction 2 has characteristic lifetime of $t_1$. In the third phase, reaction 3, the molecule shown in the lower left divides and produces the two resulting product molecules. Reaction 3 occurs with an associated lifetime of $t_2$. The photolyric process most specifically illustrated as reaction 3, effectively makes the overall reaction of FIG. 3 and included proton release irreversible.

The process step of generating released protons or other charged particles leads to changing of the pH (hydrogen ion concentration) of the sample. The degree of pH change is dependent upon the yield of the proton generating step and the concentration of the proton emitter in the sample. Exemplary pH changes are in the range from approximately 0 to approximately 1 as compared to the previous pH prior to photoactive release of the proton or other charged particle. More preferably pH changes are in the range from approximately 0.01 to 0.1. The net effect on pH due to the release of protons will typically be to decrease pH (increased acidity), although particular sample systems may demonstrate increased pH (decreased acidity) from proton emission. Alternatively, release of other types of particles, typically charged particles, through such an particle emission step may lead to either net positive or negative effects on pH.

The methods according to this invention can further include monitoring one or more optical properties of the sample during or near in time to the other method steps. For example the sample can be continuously monitored using a continuous wave laser to obtain an indication of optical properties of the sample, such as light scattering and absorbance of the sample. Additionally monitoring can occur with respect to temperature or other sample parameters. Still further the sample can be better conditioned by maintaining the sample in a desired condition, for example in a homogeneous or mixed condition. This can advantageously be done by magnetically stirring the sample within cuvette 20.

The novel methods of this invention further include measuring the stimulating electromagnetic beam pulse beamed to the sample to provide a beam pulse input energy measure indicative of the energy of the stimulating electromagnetic beam pulse beamed into the liquid sample. The measuring step can be accomplished by a variety of methods and differing measurement systems, such as the energy sensor 55 and associated energy meter 56. It is also possible to measure energy by measuring power and integrating the power rate during the stimulation pulse period.

The novel methods of this invention further include measuring the stimulating electromagnetic beam pulse passing through the sample to provide a beam pulse output energy measure indicative of the energy of the stimulating electromagnetic beam pulse which passes through the liquid sample. This measuring step can be accomplished by a variety of methods and differing measurement systems, such as the energy sensor 50. It is also possible to measure energy by measuring power and integrating the power rate during the stimulation pulse period.

The methods of this invention further include sensing acoustic output from the sample during an acoustic measurement period which follows said stimulation pulse period. Such sensing step is performed by acoustic transducer 21 in the system illustrated. Sensing of the acoustic output preferably occurs during a defined acoustic measurement period. The acoustic measurement period is preferably selected to provide selective consideration of the acoustic response which is most relevant to the analysis taking place. In most instances the acoustic measurement period will be defined to encompass periods in the range of 1 nanosecond to 100 microseconds after the stimulation pulse period ends. More preferably, the acoustic measurement period will be defined to encompass periods in the range of 10 nanosecond to 10 microseconds after the stimulation pulse period ends. The acoustic response period is the period during which the sample gives an acoustic response measured by the sensing acoustic output step. Other sensors and sensor configurations are also possible.

The methods of this invention also preferably include storing data which is indicative of the beam pulse input energy measure, beam pulse output energy measure, and the acoustic output detected during the acoustic measurement period. The testing and data storage are conducted repeatedly for each sample condition, such as 10–100 times, so that various signal noise errors and sample variations can be statistically resolved and improved measurements and analytical parameters can be determined.

Data Analysis

The novel methods of this invention produce acoustic transducer output signal data and stimulating beam energy measurement data which are further analyzed to deduce or deconvolve information which is of greater analytical value in characterizing the chemicals or chemical reactions being analyzed. The acoustic signal information, such as from transducer 21, is appropriately stored in a manner correlating it with the beam input and output energy measurements from energy sensors 55 and 50 which are applicable to the stimulating beam pulse used to induce those acoustic waves within the sample. This data is advantageously stored in oscilloscope 60, or alternatively or additionally in central controller 70.

Figure 8:
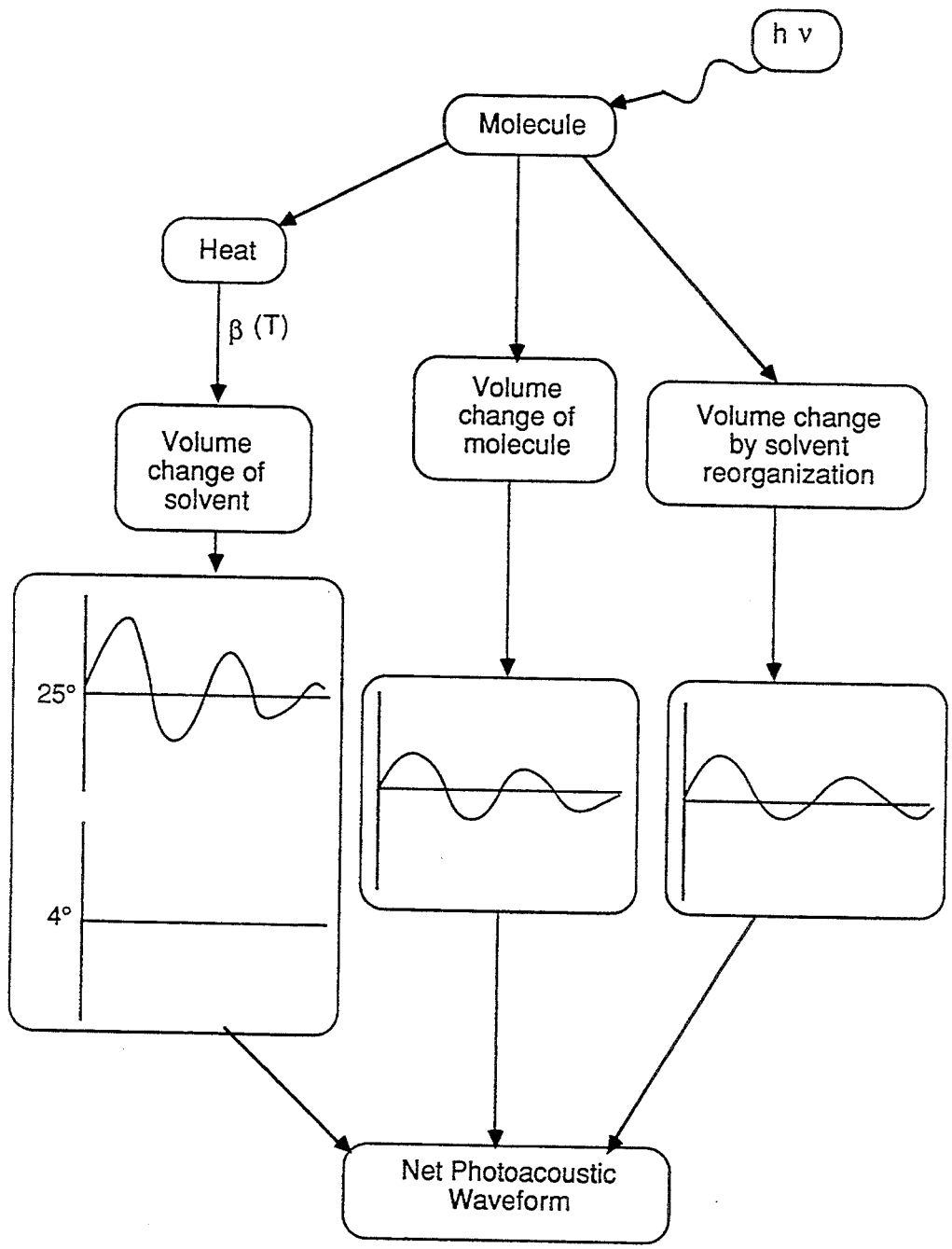
FIG. 8 is a diagram illustrating aspects of the preferred data analysis.

Central controller 70 most preferably has capabilities to also function as a data analyzer forming a part of the entire system 10. The stored data is analyzed to provide calibration for the data obtained and to provide parameters which can be used to nullify the portions of the acoustic signal which are associated with volumetric changes not relevant or desired for the analyses being conducted. For example, the acoustic pressure waves detected by transducer 21 are principally caused by volumetric changes within the sample liquid. There are three primary causes or factors leading to volumetric changes and the associated pressure waves which are generated in the sample and detected by transducer 21. The factors are: 1) volumetric changes due to heat or enthalpy changes associated with absorbance of the stimulating beam and conversion into heat; 2) volumetric changes due to changes in the volume of the molecule being tested; and, 3) volumetric changes due to electrostriction or other changes associated with solvation. FIG. 8 illustrates how the resultant signal detected by transducer 21 is a combination of or superposition of the waves generated by the three primary causes of volumetric changes within the liquid sample. The left hand or enthalpy component can be effective nullified by testing the sample system over a range of different temperatures. This is particularly important in water because the relative amplitudes of volumetric changes and resulting pressure changes are a function dependent upon the temperature of water. By running a series of tests at different temperatures with and without the chemical of interest it is possible to nullify the effects of the component of the acoustic signal attributable. to heating or other enthalpic changes caused by the stimulating beam striking the sample.

In a similar fashion the volumetric changes and associated effects on the acoustic pressure wave caused by electrostriction and any other solvation changes can be nullified. When the proton or other particle is released as a result of the stimulating beam, this brings about changes within the matrix of the solvent-solute mixture. This can be visualized as a constrictive or expansive effect tending to change the volume of the solvent forming the largest part of the liquid sample. The effects associated with volumetric solvation changes are different for different solvents and at different concentrations of the same type of solution. Thus it is possible to test a sample with a variety of different buffers and at varying solutions with and without the chemical or chemicals of interest for analysis. The released protons typically have significant and measurable effects. These effects are different for different solvent parameters. The effects with and without the chemical or chemicals of interest are compared. The testing results can then be compared to isolate the volumetric and acoustical effects associated with the solvation changes. The net effect due to electrostriction and any other solvation effects are quantified. This information is then used in data analysis of the acoustic signals generated when the samples contain the chemicals of interest. The solvation changes can then be nullified.

With information indicating the volumetric and acoustic effects associated with enthalpy changes and solvation changes, it is then possible to determine the net acoustic and volumetric effects associated with volumetric changes caused by conformational changes in the molecule of interest, or changes caused by reaction of the molecule or molecules of interest.

The data analysis used in conjunction with the methods of this invention can be carried out using analytical techniques described in greater detail in two prior articles. One is by Small, J. R. et al., entitled, "Analysis of photoacoustic waveforms using the nonlinear least squares method", *Biophysical Chemistry*, (1992) vol. 42, pp. 29–48. The other is by Small, J. R. et al., entitled "Photoacoustic determination of fluorescent quantum yields of protein probes", *SPIE Proceedings Vol. 1204—Time-Resolved Laser Spectroscopy in Biochemistry II*, (1990), pp. 126–136. Both of said articles are hereby incorporated hereinto by reference.

Deconvolution analysis used in the methods described herein is further described below. The deconvolution is preferably carried out upon the combined controller, data store and analytical computer 70. Programs preferably used therein yield $\phi_i$ (amplitude) and $\tau_i$ (lifetime) values for simultaneous or sequential exponential volume changes. Because the photoacoustic waveform of the unknown sample is always related to that of a reference compound (a reference compound absorbs a photon and converts absorbed energy to heat with unit yield in <10 ns), the recovered $\phi_i$ values have thermodynamic meaning. With careful consideration of the solvent properties giving rise to the acoustic waves 29, it is possible to calculate an actual volume change, in mL, per laser pulse, resulting from the energy decay of photoexcited molecules. Specifically, it is possible to analyze the $\phi_i$ values as a function of temperature to separate the thermal and nonthermal contributors to a particular $\phi_i$ value over a narrow temperature range (e.g., 35° C. to 15° C.). Note that examination of a sample's photoacoustic waveform at about 4° C. will tell us whether any nonthermal processes are contributing to the signal, but it is not practical to deconvolve data from that temperature. This is because a references sample, converting light to heat at a temperature at which water undergoes no thermal expansion, gives rise to little or no volume change or associated wave generation in the sample.

In order to obtain $\Delta H$ (enthalpy change) and $\Delta V_{nt}$ (the nonthermal contribution to the signal due to processes other than heat release), parameters from photoacoustic waveforms it is necessary to relate signals to temperature and other solvent physical parameters which vary with temperature. We tacitly assume that the photochemistry is not substantially altered in the temperature region of 15° to 35° C., and that most observable effects of temperature are due to highly temperature-dependent properties of the sample solvent, for example as does occur when water is the predominant sample solvent component. The $\Delta H$ and $\Delta V_{nt}$ parameters can be obtained using experimental testing according to the framework that the recovered amplitude factor, $\phi_i$, can be related to heat release q and nonthermal molecular and/or solvation volume change $\Delta V_{nt}$, by:

$$\phi_i E_{h\nu} = q + \Delta V_{nt}(C_p\rho/\beta); \tag{1}$$

where $E_{h\nu}$ is the absorbed photon energy, $C_p$ is the heat capacity, $\beta$ is the thermal volumetric expansion coefficient of the solvent, and $\rho$ is the density of the solution.

In aqueous solutions, the term $C_p\rho/\beta$ is highly temperature-dependent, primarily because of $\beta$. Based on eq. (1), a plot of $\phi E_{h\nu}$ versus $C_p\rho/\beta$ will give a line with slope of $\Delta V_{nt}$ and an intercept of q for the decay i. Theft, the enthalpy change with respect to ground state is $\Delta H = E_{h\nu} - q$.

For pure water, the parameters in the term $C_p\rho/\beta$ can be obtained from a table of values in the *CRC Handbook of Chemistry & Physics*, for example. Most biomolecules would not be handled in pure water, however, and would instead be put into a specific buffer solution. The buffer solution has different physical properties than pure water, and there is no table of data available for $C_p\rho/\beta$ for all possible buffers. However, this data can be collected and the resulting constants used. Each particular user has the freedom to experimentally determine $C_p\rho/\beta$ for any solution. A method currently used is to measure the photoacoustic waveform of a reference compound in pure water and compare it to the photoacoustic waveform of the same reference in the buffer of interest. The ratio of the amplitudes of the two references gives the ratio of the terms $\beta/C_p\rho$ for the respective solutions. Once the value for $C_p\rho/\beta$ has been obtained for a particular buffer at a particular temperature, it need not be experimentally determined again, as long as the user has access to that number at the appropriate time in the calculations.

A suitable procedure for collecting the needed data and defining relevant parameters is presented in Table I.

TABLE I

Conceptual description of measurements and analyses.
For photon energy $E_{h\nu}$ and solution (buffer and water) absorbances $A_{sam}{}^{buf}/A_{ref}{}^{buf}$, and $A_{ref}{}^{wat}$, measure photoacoustic waveforms, also noting energy/pulse of incident laser light, $E_p$, and temperature, T, of solutions.

Set T to 15° C. Collect data.

| | | | |
|---|---|---|---|
| Wave$_{ref}{}^{wat}$ | | Analyze amplitudes to give $(C_{pp}/\beta)^{buf}$ using table values of $(C_{pp}/\beta)_{wat}$* $(\phi_i E_{h\nu}, C_{pp}, \beta)$. | Result for $\tau_i$; |
| Wave$_{ref}{}^{buf}$ Wave$_{sam}{}^{buf}$ | Correct for differences in Aphd sam$^{buf}$, A$_{ref}{}^{buf}$, and in $E_p$ for each wave. | Deconvolve to give $\phi$ and $\tau_i$. | one data point |

Set T to 20° C. Collect data

| | | | |
|---|---|---|---|
| Wave$_{ref}{}^{wat}$ | | Analyze amplitudes to give $(C_{pp}/\beta)^{buf}$ using table values of $(C_{pp}/\beta)_{wat}$* $(\phi_i E_{h\nu}, C_{pp}, \beta)$. | Result for $\tau_i$; |
| Wave$_{ref}{}^{buf}$ Wave$_{sam}{}^{buf}$ | Correct for differences in Aphd sam$^{buf}$, A$_{ref}{}^{buf}$, and in $E_p$ for each wave. | Deconvolve to give $\phi$ and $\tau_i$. | one data point |

Set T to 25° C. Collect data.

| | | | |
|---|---|---|---|
| Wave$_{ref}{}^{wat}$ | | Analyze amplitudes to give $(C_{pp}/\beta)^{buf}$ using table values of $(C_{pp}/\beta)_{wat}$* $(\phi_i E_{h\nu}, C_{pp}, \beta)$. | Result for $\tau_i$; |
| Wave$_{ref}{}^{buf}$ Wave$_{sam}{}^{buf}$ | Correct for differences in Aphd sam$^{buf}$, A$_{ref}{}^{buf}$, and in $E_p$ for each wave. | Deconvolve to give $\phi$ and $\tau_i$. | one data point |

Set T to 30° C. Collect data.

| | | | |
|---|---|---|---|
| Wave$_{ref}{}^{wat}$ | | Analyze amplitudes to give $(C_{pp}/\beta)^{buf}$ using table values of $(C_{pp}/\beta)_{wat}$* $(\phi_i E_{h\nu}, C_{pp}, \beta)$. | Result for $\tau_i$; |
| Wave$_{ref}{}^{buf}$ Wave$_{sam}{}^{buf}$ | Correct for differences in Aphd sam$^{buf}$, A$_{ref}{}^{buf}$, and in $E_p$ for each wave. | Deconvolve to give $\phi$ and $\tau_i$. | one data point |

Set T to 35° C. Collect data.

| | | | |
|---|---|---|---|
| Wave$_{ref}{}^{wat}$ | | Analyze amplitudes to give $(C_{pp}/\beta)^{buf}$ using table values of $(C_{pp}/\beta)_{wat}$* $(\phi_i E_{h\nu}, C_{pp}, \beta)$. | Result for $\tau_i$; |
| Wave$_{ref}{}^{buf}$ Wave$_{sam}{}^{buf}$ | Correct for differences in Aphd sam$^{buf}$, A$_{ref}{}^{buf}$, and in $E_p$ for each wave. | Deconvolve to give $\phi$ and $\tau_i$. | one data point |

Make plot.
Take data points and plot $\phi_i E_{h\nu}$ vs. $C_{pp}/\beta$. Calculate slope and intercept to obtain $\Delta V_{nt}$ and q for decay i. Caculate enthalpy of intermediate arising from decay i by $\Delta H = E_{h\nu} \cdot q$.
Collect more data, varying the buffer.
To discern whether protons are involved in the photoreactions, perform all of the above measurements systematically for solutions using each of three buffers: Tris, cacodylate, and phosphate. These buffers give different, known, $\Delta V_{sol}$ values which will give predictable changes in the $\Delta V_{nt}$ obtained above.
Conclude:
If $\Delta V_{nt}$ varies predictably with buffer type, then protons are involved in decay i, and most likely $\Delta V_{nt} = \Delta V_{sol}$, a volume change due to solvent electrostriction effects.
If $\Delta V_{nt}$ is independent of buffer type, then no protons are involved, and most likely $\Delta V_{nt} = \Delta V_{con}$, a photoinduced molecular conformational volume change.
A diagnostic test for photoinduced electron release as a contributor to $\Delta V_{nt}$ is currently under development.

In Table I, the italicized parameters are those which must be obtained experimentally, e.g. photon energy $E_{hv}$, solution (buffer and water) absorbances of the sample and references $A_{sam}{}^{buf}$, $A_{ref}{}^{buf}$, and $A_{ref}{}^{wat}$, measured photoacoustic waveforms $Wave_{ref}{}^{wat}$, $Wave_{ref}{}^{buf}$, $Wave_{sam}{}^{buf}$; the average energy per pulse of incident laser light, $E_p$, and temperature, T, of solutions. Also indicated are the calculations needed in order to recover $\Delta H$, $\Delta V_{nt}$ and $\tau$ for resolvable decays from photoacoustic data. Table I assumes that there is no $C_p\rho/\beta$ data available for the buffer used. Therefore, it includes using CRC tabular $C_p\rho/\beta$ data for pure water, and then calculating the $C_p\rho/\beta$ data for pure water, and then calculating the $C_p\rho/\beta$ data for the buffer used given the amplitudes of $Wave_{ref}{}^{wat}$, $Wave_{ref}{}^{buf}$.

Table I also indicates how, if there is a $\Delta V_{nt}$ component apparent after data points are plotted (easily apparent by a nonzero slope), the user could determine whether protons and their solvation are responsible for the nonthermal signal. This process involves repeating the whole series of measurements and calculations for different buffers with different volume changes upon protonation. If the photoacoustic signals are the same irrespective of buffer identity, then no protons are released to or removed from solution on the time scale of the experiment. If protons are involved, however, then different buffers will give dramatically different photoacoustic signals.

The complexity of Table I demonstrates the need for systematic data analysis and reduction of photoacoustic waveform data to obtain the ultimate parameters, $\Delta H$, $\Delta V_{nt}$, and $\tau_i$. Deconvolution of waveforms yields $\phi_i$ and $\tau_i$; another level of data reduction yields $\Delta H$, $\Delta V_{nt}$, and $\tau_i$; and yet another level potentially yields $\Delta H$, $\Delta V_{con}$ and/or $\Delta V_{sol}$, and $\tau_i$. Previously, it has been common to have analytical programs which take raw data, process the data, then deconvolve the data to obtain $\phi_i$ and $\tau_i$ values. It is then up to the user to perform the remaining shells of calculations to break $\phi_i$ values into $\Delta H$ and $\Delta V_{nt}$ values, and potentially break $\Delta V_{nt}$ values into molecular conformational change values ($\Delta V_{con}$) and solvation of proton values ($\Delta V_{sol}$).

Example 1

Analysis of Pyranine

The methods of this invention were used to analyze the effect of proton instigated pH changes during the nanosecond to microsecond time frames. Pyranine is a more common name for the compound 8-hydroxypyrene-1,3,6-trisulfonic acid. Pyranine is a fluorophore and is also referred to by the acronym HPTS.

Sample liquids were prepared using pure water and Tris, phosphate, and cacodylate buffers. Pyranine was included in the samples as the proton-emitting compound. The samples were analyzed using the methods of this invention. Volume changes associated with protonation of the buffers without pyranine are known from prior measurements. This example involved measurement of the actual change in enthalpy $\Delta H$ of the system.

A single hydroxyl group forming a part of pyranine is known to reversibly release a proton into solution upon photoexcitation. The relevant photochemical reactions are simplistically given by eqs. (2) to (6), where Pyr—OH designates a molecule of pyranine, and Buf designates a buffer species (charged or uncharged). Eqs. (2) to (6) focus only on photon-induced chemical reactions, and do not attempt to describe the complete photophysics of this pH-sensitive fluorescent dye.

$$Pyr\text{—}OH + h\nu \rightarrow Pyr\text{—}OH^* \qquad (2)$$

$$Pyr\text{—}OH^* \rightarrow Pyr\text{—}O_- + H_+ \qquad (3)$$

$$Buf + H_+ \rightarrow BufH_+ \qquad (4a)$$

$$H^2O + H_+ \rightarrow H^3O_+ \qquad (4b)$$

$$BufH_+ \rightarrow Buf + H_+ \qquad (5a)$$

$$H^3O_+ \rightarrow H^2O + H_+ \qquad (5b)$$

$$Pyr\text{—}O_- + H_+ \rightarrow Pyr\text{—}OH \qquad (6)$$

Stimulation was conducted using a system similar to that described hereinabove. Stimulation by a photon of laser light is represented in eq. (2). Due to the very low excited-state $pK_a{}^*$ ($\sim$0.4) of the hydroxyl group on pyranine, a proton is released to solution, eq. (3). During this time period, the original population of photoexcited molecules relaxes back to electronic ground state conditions. The H$^+$ released in eq. (3) reacts with either buffer species or water, eqs. (4a) and (4b). Later, with the ground-state pyranine molecules back to their normal $pK_a$ of around 7.8, the reverse protonation occurs. Protons are released from buffer or water, eqs. (5a) and (5b), and react with the pyranine anion, eq. (6). No net photochemistry occurs. Energetically, absorbed photon energy is converted partly to fluorescent light (not indicated above), with the remainder to heat. Reactions (2)–(4) are fast, occurring within approximately a 10 nanosecond (ns) time period. Reactions (5) and (6) are expected to occur more slowly, potentially resolvable on the nanosecond to microsecond time scale.

The protonation or deprotonation of a buffer species, eqs. (4a) or (5a), may be accompanied by a substantial volume change of solution. For example, the reaction:

$$H^+ + HPO_4{}^{2-} \rightarrow H_2PO_4{}^- \qquad (7)$$

is accompanied by a volume increase $\Delta V = 24$ mL/mol. In reaction (7), the number of charges is reduced from 3 (1 positive, 2 negative) to 1 (negative), with concomitant release of the densely bound, "electrostricted" water molecules from the charged groups. The protonation of neutral Tria results in the overall loss of 0 charges; its $\Delta V$ upon protonation having been previously measured as 1 mL/mol.

The sample compound, pyranine was dissolved in each of four solvents: deionized water; 0.1M sodium phosphate buffer pH 7.0; 0.1M Tris-HCl buffer pH 7.0; and, 0.1M sodium cacodylate buffer pH 7.0. Metmyoglobin serves as a reference compound. Sample absorbances were in the range of 0.78 to 0.85 at 366.6 nm (1-cm path length). Photoacoustic measurements were made similar to those described previously, using a nitrogen-pumped dye laser and a Panametrics V103 piezoelectric transducer for detection. Waveforms were digitized at 10 nanosecond intervals. Data from 250 laser pulses were averaged to give one waveform. Approximately 5 $\mu J$ of 366.6 nm light was incident on the cuvette with each pulse. The light transmitted from the cuvette was measured with a second energy meter probe in order to calculate the in situ absorbance of the sample.

The analysis was broken into two main routines. First, at each temperature (temperature range of approximately 15° to 35° C. in 2.5° C. intervals, temperature was measured in the cuvette), the photoacoustic waveform of the reference compound, metmyoglobin, in water was compared to the waveforms of the reference compound dissolved in each of the buffer solutions. This allows measurement of the $C_p\angle\rho/\beta$ values for each of the buffers at each temperature. Then, at each temperature (approximately 17.5°, 22.5° and 27.5° C.), the photoacoustic waveforms of the reference compound, metmyoglobin, and the sample compound, pyranine, both in the same solution type, were measured. The matched pairs of reference and sample waveforms in water or buffer were processed and deconvolved to yield amplitude ($\phi_i$) and lifetime ($\tau_i$) pairs of data for subsequent analysis for $\Delta H$ and $\Delta V_{nt}$. Analyses were done using; a computer programmed with appropriate analytical software.

Figure 9:
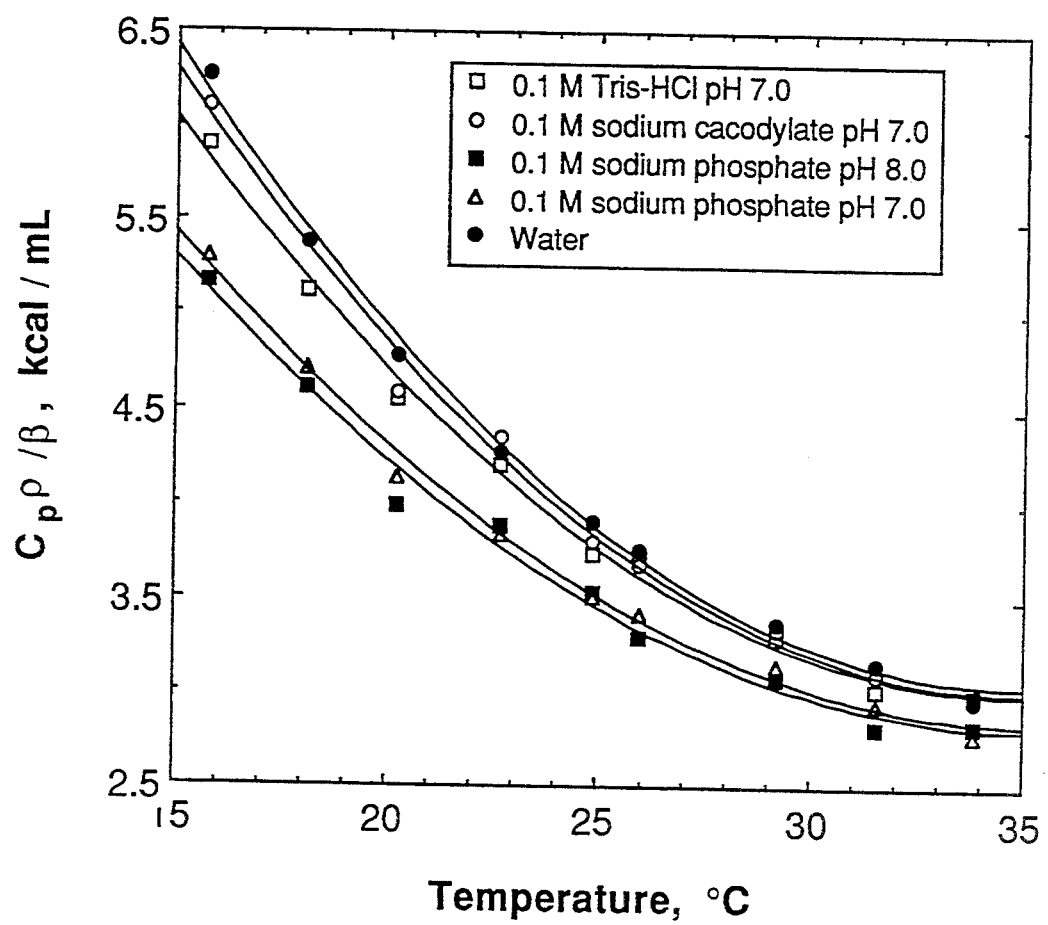
Figure 11:
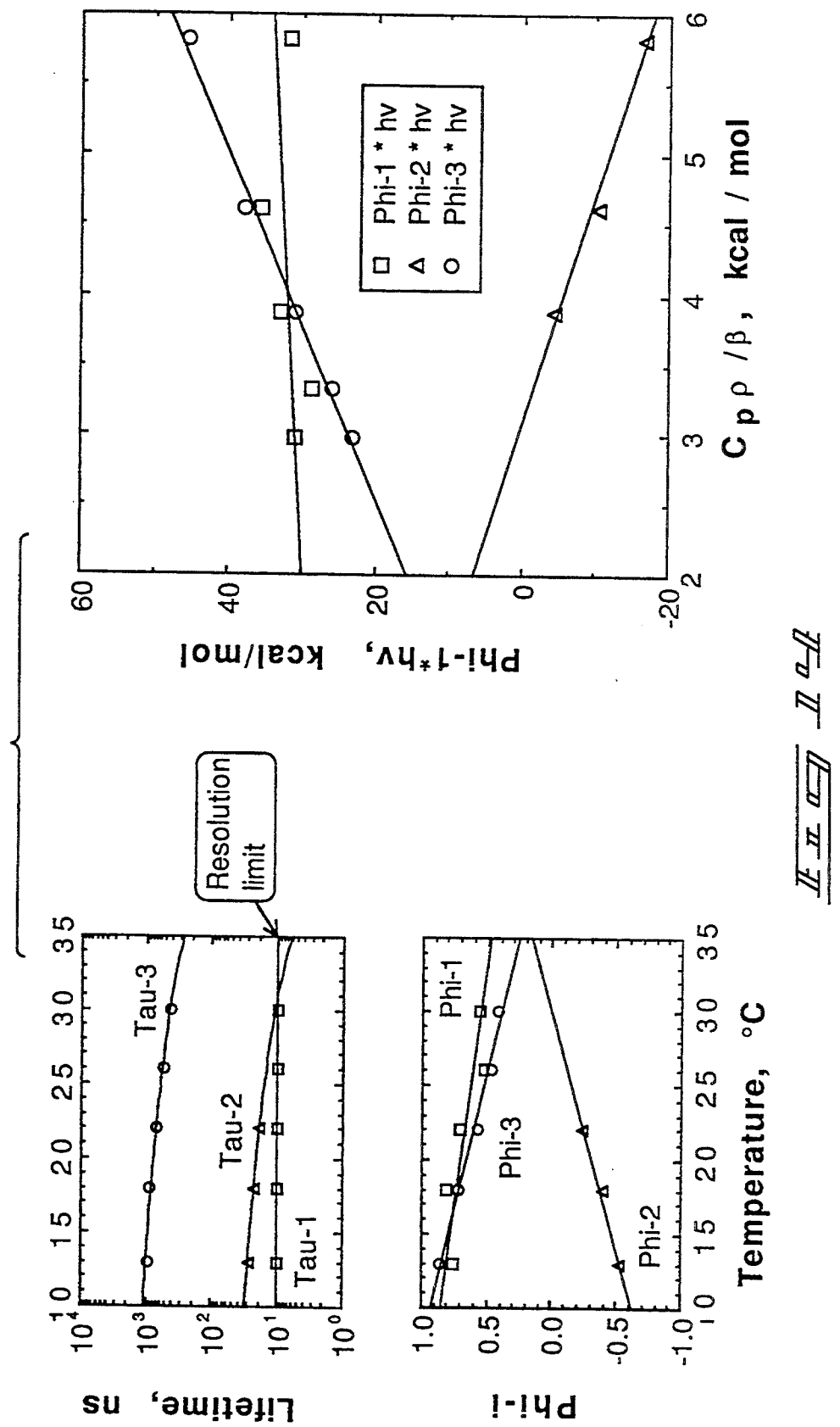

FIG. 9 shows the measured $C_p\rho/\beta$ values for each of the buffers at each temperature. The buffer values were computed using photoacoustic waveform amplitudes of metmyoglobin in buffer compared to metmyoglobin in water. FIG. 10 shows the relative photoacoustic waveforms (corrected for slight pulse-to-pulse energy and sample absorbance differences) for metmyoglobin (the reference compound) and pyranine (the sample compound) in a variety of solution conditions at 27.0° C. Note that while the metmyoglobin waveform has approximately the same shape no matter which solution condition is used, the pyranine waveform varies greatly in shape. Deconvolution of the photoacoustic data yielded results such as those shown in FIG. 11. In each case, two decays were resolved: one fast (<20 ns) and the other slower (0.1 to 0.4 µs, depending on solvent). The amplitude factors ($\phi_i$ values) for the fast (i=1) and slow (i=2) decays were substantially different and included some large negative values. Thus, the somewhat odd shapes of the pyranine waveforms in water and Tris buffers in FIG. 10 are due to the fact that a substantial negative waveform is added to a substantial positive waveform. To analyze the meaning of the $\phi_i$ values, standard plots were made in FIG. 12 involving recovered $\phi_i$ values, the photon energy $h\nu$ (for 366.6 nm, this is 78.0 kcal/mol), and the solvent physical parameters $C_p\rho/\beta$ (obtained in FIG. 9) which are strongly dependent on temperature. From the slope and intercept of the lines in FIG. 12, the data in Table I are obtained.

Some of the interesting features of the data in Table I are presented in FIG. 13, in which enthalpy changes are shown as $\Delta H_1 = h\nu - q_1$ for stage 2, $\Delta H_{1+2} = h\nu - (q_1+q_2)$ for stage 3, and volume changes are shown as $\Delta V_1$ and ($\Delta V_1 + \Delta V_2$) for stages 2 and 3, respectively. In each case, photon absorption (stage 1) leads to excited-state pyranine molecules or anions, depending on the starting pH. Within about 20 ns, the excited species have decayed to a state (stage 2) which exhibits a volume change relative to the species before photon absorption. Since the volume changes parallel the known volume changes which occur upon protonating phosphate, Tris and cacodylate, the protons are released and equilibrate with the buffer in the fast step (i=1), consistent with the known rapid photoinduced proton release of pyranine. Importantly, in the second step ($\tau_2 = 0.1$ to 0.4 µs), the opposite volume change occurs relative to the first step (i.e., $\Delta V_1 \approx -\Delta V_2$). This suggests that the second step involves the return of a proton to the pyranine anion, consistent with the known photochemistry of pyranine. When the photochemistry is complete, and all pyranine species have returned to their equilibrium ground state populations, there should be little difference observed between the solutions as evidenced by photoacoustic data. FIG. 13 shows that at the end of the second resolved decay (stage 3 in FIG. 13), all four solutions are at the same stage, with $q_1+q_2 \approx 31$ kcal/mol (mol of photoexcited molecules) of heat having been released to solution, and a net volume change of about zero mLmol relative to the preexcitation stage. The result that $q_1+q_2 \neq h\nu$ is indicative of some laser photon energy being converted into fluorescent light, as expected for the fluorescent pyranine. There is some possibility that some laser photon energy is tied up in a long-lived ($\tau > 10$ µs) species.

The photochemistry of pyranine in water gave rise to an initial strongly negative $\Delta V_1 = -24.5$ mL/mol. This added to the buffer $\Delta V_1$ values are offset from the literature protonation volume change values by a consistent negative amount ($-11$ to $-16$ mL/mol). Therefore this is suggestive that the observed offset means that some released protons react with buffer molecules while others are solvated by water.

TABLE II

| Decay | Parameter | 0.1 M Phosphate pH 7 | 0.1 M Cacodylate pH 7 |
|---|---|---|---|
| 1 | q1 | 9.4 kcal/mol | 26.6 kcal/mol |
| 1 | $\Delta V_1$ | +13.4 mL/mol | −2.9 mL/mol |
| 2 | q2 | 20.8 kcal/mol | 6.7 kcal/mol |
| 2 | $\Delta V_2$ | −14.6 mL/mol | +1.6 mL/mol |
| 1+2 | q1+q2 | 30.2 kcal/mol | 33.3 kcal/mol |
| 1+2 | $\Delta V_1 + \Delta V_2$ | −1.2 mL/mol | −1.3 mL/mol |

| Decay | Parameter | 0.1 M Tris-HCl pH 7 | [no pH stabilization] |
|---|---|---|---|
| 1 | q1 | 24.6 kcal/mol | 52.6 kcal/mol |
| 1 | $\Delta V_1$ | −11.9 mL/mol | −24.5 mL/mol |
| 2 | q2 | 0.8 kcal/mol | −17.3 kcal/mol |
| 2 | $\Delta V_2$ | +13.2 mL/mol | +18.7 mL/mol |
| 1+2 | q1+q2 | 25.4 kcal/mol | 35.3 kcal/mol |
| 1+2 | $\Delta V_1 + \Delta V_2$ | 1.3 mL/mol | −5.8 mL/mol |

Literature $\Delta V_{lit}$ for protonation of buffers:[10]

24 mL/mol    13.2 mL/mol
−1 mL/mol

Difference from literature values ($\Delta V_1 - \Delta V_{lit}$):

−11 mL/mol    −16 mL/mol
−11 mL/mol

Example 2

Analysis of the Photoreactions of Carboxymyoglobin

The photoactive CO complex of myoglobin, MbCO, was studied to see if the Fe—CO bond strength in MbCO can be measured in the presence of molecular conformational changes in the protein following photodissociation of the ligand. The rapid Fe—CO bond cleavage will be the most rapid event in the experiment and will fall into the "fast" category of $\tau_1 < 10$ ns, the time-resolution limit of the experiment. Subsequent decays reflect the relaxation of the protein to its equilibrium deligated (dcoxyMb) stage.

Pulsed-laser photoacoustic measurements were done essentially as described above. Photoexcitation was achieved with 520 nm laser light, 10 µJ pulses were incident on the sample cuvette, data from 100 pulses were averaged per waveform, and sample absorbances were in the range of 0.8 to 1.0. The instrument was initially tested to determine that signals were linear with pulse energy. MbCO samples were prepared by dissolving the metmyoglobin in 0.1M phosphate buffer, pH 8.0. Photoacoustic measurements were made with gentle argon flow into the air space of the cuvette. Solvent $C_p\rho/\beta$ values were obtained from FIG. 9. Deconvolution results were in agreement using both nonlinear least squares analysis and the Method of Moments.

Either lowering the sample temperature below, 25° C., or increasing solvent viscosity by adding glycerol result in a third decay component emerging from analysis of pulsed-laser photoacoustic data from MbCO. The temperature effect is seen in FIG. 14. Above 25° C., the middle lifetime merges with the fast lifetime, such that both are at or below the resolution limit of 10 ns (here, defined as the digitization channel width, which is set to 10 ns). Because $\tau_1$ and $\tau_2$ are so close together, there is more uncertainty in $\phi_1$ and $\phi_2$. The values obtained in the analysis of the $\phi_i$ values, FIG. 14, are reported in Table III along with literature values for sperm whale and horse MbCO.

There are conclusions which can be drawn from the data. Notable is the appearance of large conformational volume changes of the protein accompanying the 20–80 ns decay (from +1 to −7 mL/mol for our sperm whale MbCO data) and the 0.7–1.0 µs decay (from −7 to +4 mL/mol) following photolysis of the Fe—CO bond. The source of the volume change is not due to solvent electrostriction of protons, since identical results have been found for MbCO in both Tris and phosphate buffers. The $\tau_2 = 0.7$–1.0 µs volume change is especially important, since it has not yet been observed by spectroscopic methods monitoring specific chromophores for spectral perturbations. In addition, our preliminary value of +28 kcal/mol for the enthalpy difference between ground state MbCO and the intermediate state existing 10 ns following Fe—CO bond photolysis agrees well with the value of $21 \pm 2$ kcal/mol found for horse MbCO using picosecond phase grating spectroscopy.

TABLE III

Comparison of sperm whale and horse MbCO following photolysis of Fe-CO bond.
$\Delta H_i$ and $\Delta V_i$ values refer to the enthalpy or volume difference between the intermediate state formed by decay i, and the original ground state MbCO. In our study, $\Delta H_j = h\nu \cdot q_i$, with $h\nu = 55.0$ kcal/mol (520 nm light).

| MbCO source | | Sperm Whale | | Horse |
|---|---|---|---|---|
| Components resolved | 3 (this preliminary study) | 2 (1990, Westrick, Peters et al.)[17] | 2 (1990, Westrick & Peters)[16] | 3 (1993, Norris & Peters)[9] |
| $\Delta H_1$ $\tau_1 = 10$ ns | 28 kcal/mol | [not resolved] | [not resolved] | 10.0 ± 2.6 kcal/mol |
| $\Delta H_{1+2}$ ($\tau_2 = 20$-80 ns) | 6 kcal/mol | 0.8 ± 1.4 kcal/mol | 7.4 ± 2.0 kcal/mol | 6.2 ± 0.7 kcal/mol |
| $\Delta H_{1+2+3}$ ($\tau_3 = 0.7$-1.0 µs) | 10 kcal/mol | 9.9 ± 2.0 kcal/mol | 14.3 ± 2.9 kcal/mol | 16 ± 14 kcal/mol |
| $\Delta V_1$ ($\tau_1 = 10$ ns) | 1 mL/mol | [not resolved] | [not resolved] | 0.8 ± 0.6 mL/mol |
| $\Delta V_{1+2}$ ($\tau_2 = 20$-80 ns) | −7 mL/mol | −9.0 ± 0.3 mL/mol | −1.7 ± 0.5 mL/mol | −1.91 ± 0.16 mL/mol |
| $\Delta V_{1+2+3}$ ($\tau_3 = 0.7$-1.0 µs) | 4 mL/mol | 5.1 ± 0.5 mL/mol | 13.8 ± 0.7 mL/mol | 13 ± 3 mL/mol |

Example 3

Analysis of Photolabile Compound—2-hydroxyphenyl 2-nitrophenylethyl phosphate Time-resolved, pulsed-laser photoacoustic measurements were made at 25° C. using the 366.6 mn output of a nitrogen-pumped dye laser, with detection provided by a 1.0-MHz broadband ultrasonic transducer, and signals digitized at 10 ns per channel. With horse skeletal metmyoglobin (metMb) serving as a reference compound, photoacoustic signals from compound 1 (2-hydroxyphenyl 2-nitrophenylethyl phosphate) and compound 2 (pyranine) were analyzed by nonlinear least squares to yield $\phi, \tau$ (amplitude,lifetime) pairs of values for each measurable photoinduced volume change.

Figure 15:
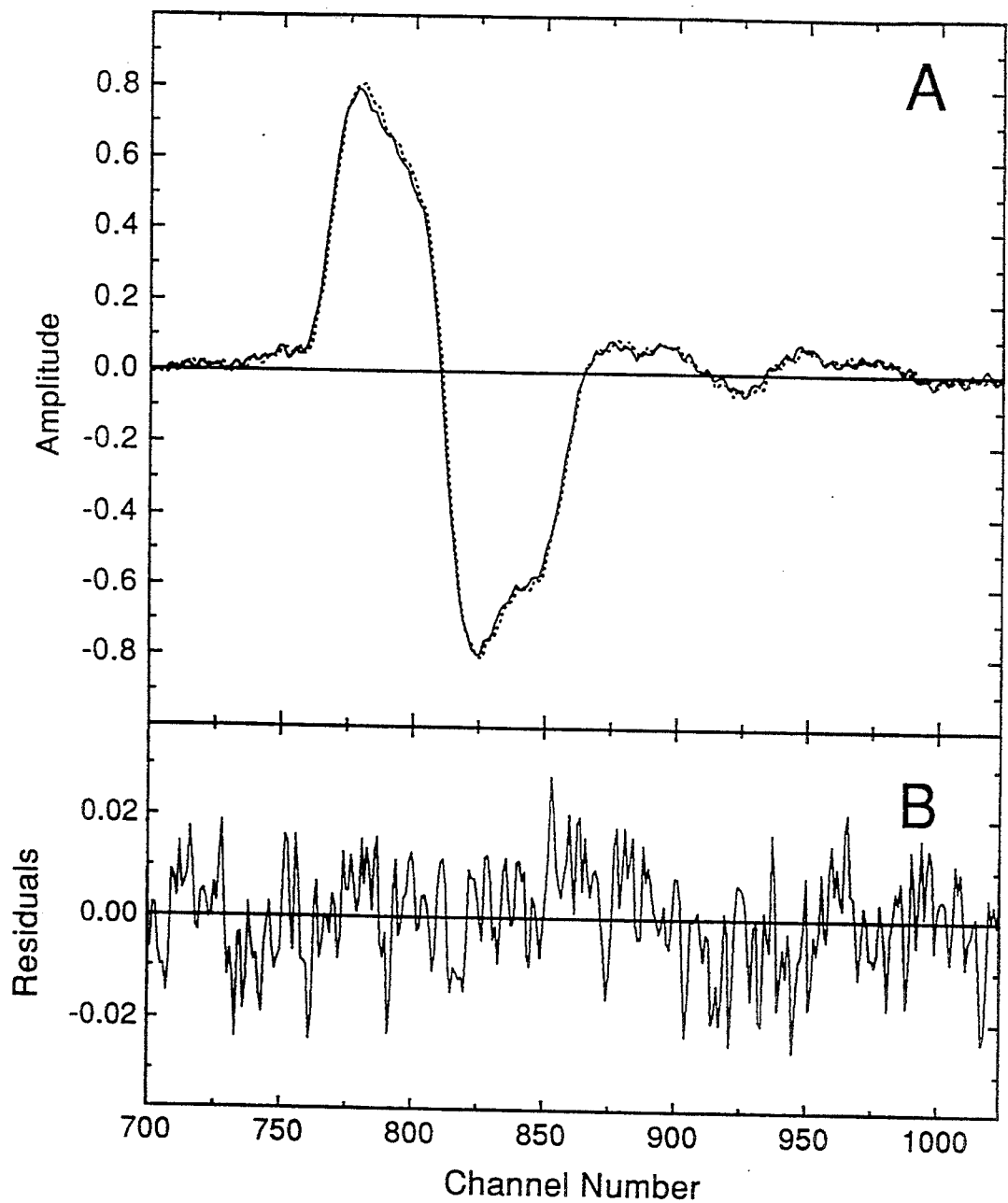

The photolabile compound named above in the subtitle (compound 1) showed one principal photoinduced volume change when dissolved in 45 mM buffer, 45 mM KCl, pH 7.4, buffer=phosphate, cacodylate, or Tris-HCl (FIG. 15, part A). This volume change was faster than the digitizing channel width of the experiment, 10 ns, and probably reflects both thermal expansion of the solution due to heat release following photoexcitation, as well as solvent electrostriction changes. The latter contribution is indicated by the data in FIG. 16, showing a strong dependence of the amplitude of the photoacoustic waveform ($\phi$ value) on the identity (and thus $\Delta V_p$) of the buffer used. The positive slope of the curve in FIG. 16 suggests that a proton is released by compound 1 within 10 ns of photoexcitation. Within the resolvable time window of the experiment (10 ns–10 µs), very little further reaction is discerned.

Compound 1 shows rapid proton release and no subsequent reprotonation within the observation window of the experiment. The extent of proton release per laser flash is estimated as follows. The solution volume illuminated by the laser flash is ~50 µL. With the dye laser output at 366.6 nm and a 5 µJ pulse incident on the 1-cm cuvette with solution optical density (OD=0.8), about 5 pmol of $H^+$ are released. At pH 7, there are 5 pmol of $H^+$ in the illuminated volume to start with. This corresponds to a transient $[H^+]$ increase of $1 \times 10^{-7}$M. The observed photoacoustic signal is likely to be due to two volume changes summing together: the electrostriction volume change, and the volume change due to heat release to the solvent. These two sources can be separated and quantified by studying the temperature dependence of the signals, especially near 4° C., where the thermal expansion coefficient of water is zero, and signals observed can only be due to other volume changes besides heat release.

Throughout these studies, metMb was used as the reference compound. The reference compound is one which absorbs light, then totally and rapidly converts the light energy to heat. For the reference compound, under the same experimental conditions described above, approximately 1ucal of heat is released to solution per pulse, resulting in a temperature increase in the illuminated volume of $\sim 10^{-4}$° C., and a volume change (at 25° C.) of $\sim 10^{-10}$ mL. The $10^{-10}$ mL/pulse expansion is what generates the pressure waves detectable by the acoustic transducer. Accordingly, the photoacoustic experiment is sensitive enough to measure protein conformational changes, heat changes and electrostriction changes.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for analyzing chemical reactions, comprising:
    preparing a liquid sample having:
        a protic liquid solvent;
        at least one primary reactant; and,
        a photoactive particle-emitting compound different from said at least one primary reactant; said photoactive particle-emitting compound being a molecular or ionic species having at least a chromophoric group and a charged-particle group; said chromophoric group having atoms and associated bonds such that said chromophoric group absorbs a stimulating electromagnetic beam pulse to release at least one active charged particle; said charged-particle group upon division from the chromophoric group forming a charged particle which acts as a secondary reactant which reacts with the primary reactant; said charged-particle group being substantially non-reactive with said at least one primary reactant until divided from the chromophoric group by a stimulating electromagnetic beam pulse;
    beaming a stimulating electromagnetic beam pulse onto the liquid sample during a stimulation pulse period of time; said stimulation pulse period having a duration in the range of approximately $10^{-10}$ to approximately $10^{-7}$ seconds; said beaming being accomplished using a thin substantially planar beam shape having beam sidewall faces;
    generating charged particles from said particle-emitting compound contained within said sample;
    reacting the released charged particles with the primary reactant during a period from approximately 1 nanosecond to 10 microseconds after said stimulation pulse period of time;
    measuring the stimulating electromagnetic beam pulse to the sample to provide a beam pulse input energy measure indicative of the energy of the stimulating electromagnetic beam pulse beamed into the liquid sample;
    measuring any stimulating electromagnetic beam pulse which passes through the sample to provide a beam pulse output energy measure indicative of the energy of the stimulating electromagnetic beam pulse which passes through the liquid sample;
    sensing acoustic output from the sample during an acoustic measuring period which follows said stimulation pulse period; said acoustic measuring period being from approximately 1 nanosecond to 10 microseconds after said stimulation pulse period of time; said sensing being accomplished with a transducer oriented to face the beam sidewall faces;
    storing data indicative of the beam pulse input energy measure, beam pulse output energy measure, and acoustic output during the acoustic measuring period.

2. A method for analyzing chemical reactions according to claim 1 wherein said particle-emitting compound results in a charged particle which is a proton, a hydroxide ion, or molecular or ionic species with an active proton or hydroxide ion included thereon.

3. A method for analyzing chemical reactions according to claim 1 wherein said beaming involves beam pulses having energies in the range of approximately $10^{-1}$ to approximately $10^1$ microjoules per microliter of illuminated sample.

4. A method for analyzing chemical reactions according to claim 1 wherein said particle-emitting compound are selected from the group consisting of 2-hydroxyphenyl 2-nitrophenylethyl phosphate, sodium salt; adenosine-5'-triphosphate, 3—O—(1-(-2-nitrophenyl)ethyl) ester, disodium salt; 1-(2-nitrophenyl)ethyl phosphate; 3',5'-dimethoxybenzoin phosphate; and fluorescein-bis-4,5-dimethoxy-2-nitrobenzyl ether.

5. A method for analyzing conformational changes in a biological molecule of interest, comprising:
    preparing a liquid sample having:
        a protic liquid solvent;
        at least one biological molecule; and,
        a photoactive particle-emitting compound different from said biological molecule; said photoactive particle-emitting compound being a molecular or ionic species having at least a chromophoric group and a charged-particle group; said chromophoric group comprising atoms and associated bonds such that said chromophoric group absorbs said stimulating electromagnetic beam pulse to release at least one active charged particle; said charged particle upon division from the chromophoric group causing a pH change which affects the biological molecule; said charged-particle group being relatively less available to affect the pH of the liquid sample until the charged particle is divided from the chromophoric group by a stimulating electromagnetic beam pulse;

beaming a stimulating electromagnetic beam pulse onto the liquid sample during a stimulation pulse period of time;

generating charged particles from said particle-emitting compound contained within said sample;

changing the pH of the liquid sample due to said generation of charged particles;

measuring the stimulating electromagnetic beam pulse to the sample to provide a beam pulse input energy measure indicative of the energy of the stimulating electromagnetic beam pulse beamed into the liquid sample;

measuring any stimulating electromagnetic beam pulse which passes through the sample to provide a beam pulse output energy measure indicative of the energy of the stimulating electromagnetic beam pulse which passes through the liquid sample;

sensing acoustic output from the sample during an acoustic measuring period which follows said stimulation pulse period;

storing data indicative of the beam pulse input energy measure, beam pulse output energy measure, and acoustic output during the acoustic measuring period.

6. A method for analyzing chemical reactions according to claim 5 wherein said particle-emitting compound results in a charged particle which is a proton, a hydroxide ion, or molecular or ionic species with an active proton or hydroxide ion included thereon.

7. A method for analyzing chemical reactions according to claim 5 wherein said beaming involves beam pulses having energies in the range of approximately $10^{-1}$ to approximately $10^1$ microjoules per microliter of illuminated sample.

8. A method for analyzing chemical reactions according to claim 5 wherein said particle-emitting compound is selected from the group consisting of 2-hydroxyphenyl 2-nitrophenylethyl phosphate, sodium salt; adenosine-5'-triphosphate, 3—O—(1-(-2-nitrophenyl)ethyl) ester, disodium salt; 1-(2-nitrophenyl)ethyl phosphate; 3',5'-dimethoxybenzoin phosphate; and fluorescein-bis-4,5-dimethoxy-2-nitrobenzyl ether.

9. A method for analyzing chemical reactions, comprising:

preparing a liquid sample having:
a protic liquid solvent;
at least one primary reactant; and,
a photoactive particle-emitting compound different from said at least one primary reactant; said photoactive particle-emitting compound being a molecular or ionic species having a chromophoric group with atoms and associated bonds such that said chromophoric group absorbs said stimulating electromagnetic beam pulse to release at least one active charged particle;

providing said particle-emitting compound in the liquid sample; said particle-emitting compound having said chromophoric group, and a particle group which upon division from the chromophoric group becomes a charged particle which acts as a secondary reactant which reacts with the primary reactant; said particle group being substantially non-reactive with said at least one primary reactant until divided from the chromophoric group by a stimulating electromagnetic beam pulse;

beaming a stimulating electromagnetic beam pulse onto the liquid sample during a stimulation pulse period of time;

generating charged particles from said particle-emitting compound contained within said sample;

reacting the released charged particles with the primary reactant;

measuring the stimulating electromagnetic beam pulse to the sample to provide a beam pulse input energy measure indicative of the energy of the stimulating electromagnetic beam pulse beamed into the liquid sample;

measuring any stimulating electromagnetic beam pulse which passes through the sample to provide a beam pulse output energy measure indicative of the energy of the stimulating electromagnetic beam pulse which passes through the liquid sample;

sensing acoustic output from the sample during an acoustic measuring period which follows said stimulation pulse period;

storing data indicative of the beam pulse input energy measure, beam pulse output energy measure, and acoustic output during the acoustic measuring period.

10. A method for analyzing chemical reactions according to claim 9 wherein said particle-emitting compound results in a charged particle which is a proton, a hydroxide ion, or molecular or ionic species with an active proton or hydroxide ion included thereon.

11. A method for analyzing chemical reactions according to claim 9 wherein said beaming involves beam pulses having energies in the range of approximately $10^{-1}$ to approximately $10^1$ microjoules per microliter of illuminated sample.

12. A method for analyzing chemical reactions according to claim 9 wherein said particle-emitting compound are selected from the group consisting of 2-hydroxyphenyl 2-nitrophenylethyl phosphate, sodium salt; adenosine-5'-triphosphate, 3—O—(1-(-2-nitrophenyl)ethyl) ester, disodium salt; 1-(2-nitrophenyl)ethyl phosphate; 3',5'-dimethoxybenzoin phosphate; and fluorescein-bis-4,5-dimethoxy-2-nitrobenzyl ether.

* * * * *